(12) United States Patent
Beira et al.

(10) Patent No.: US 9,696,700 B2
(45) Date of Patent: Jul. 4, 2017

(54) MECHANICAL TELEOPERATED DEVICE FOR REMOTE MANIPULATION

(75) Inventors: Ricardo Beira, Lausanne (CH); Lionel Flaction, Chavannes-pres-Renens (CH)

(73) Assignee: Ecole Polytechnique Federale De Lausanne, Lausanne (CH)

( * ) Notice: Subject to any disclaimer, the term of this patent is extended or adjusted under 35 U.S.C. 154(b) by 587 days.

(21) Appl. No.: 14/233,184

(22) PCT Filed: Jul. 25, 2012

(86) PCT No.: PCT/IB2012/053786
§ 371 (c)(1),
(2), (4) Date: Jan. 16, 2014

(87) PCT Pub. No.: WO2013/014621
PCT Pub. Date: Jan. 31, 2013

(65) Prior Publication Data
US 2014/0195010 A1    Jul. 10, 2014

Related U.S. Application Data

(60) Provisional application No. 61/511,994, filed on Jul. 27, 2011.

(30) Foreign Application Priority Data

May 18, 2012    (CH) .......................................... 702/12

(51) Int. Cl.
*G05B 19/18* (2006.01)
*G05B 15/02* (2006.01)
(Continued)

(52) U.S. Cl.
CPC ........ *G05B 15/02* (2013.01); *A61B 17/00234* (2013.01); *A61B 17/29* (2013.01);
(Continued)

(58) Field of Classification Search
CPC .. G05B 15/02; B25J 13/02; B25J 3/02; A61B 17/29; A61B 17/00234; A61B 2090/506; A61B 2034/715; A61B 2017/291
(Continued)

(56) References Cited

U.S. PATENT DOCUMENTS 2,774,488 A    12/1956    Goertz et al.
4,756,655 A    7/1988    Jameson
(Continued)

FOREIGN PATENT DOCUMENTS

JP    2009018027 A    1/2009
SU    722754    3/1980
(Continued)

OTHER PUBLICATIONS

Chinese Application No. 201280037626.9 filed Jan. 27, 2014.
(Continued)

*Primary Examiner* — Ziaul Karim
(74) *Attorney, Agent, or Firm* — Foley & Lardner LLP

(57) ABSTRACT

A mechanical teleoperated device for remote manipulation includes a slave unit having a number of slave links interconnected by a plurality of slave joints; an end-effector connected to the slave unit; a master unit having a corresponding number of master links interconnected by a plurality of master joints; and a handle connected to a distal end of the master unit. The device further includes first device arranged to kinematically connect the slave unit with the master unit, second device arranged to kinematically connect the end-effector with the handle, and a mechanical constraint device configured to ensure that one master link of the master unit is guided along its longitudinal axis so that the corresponding slave link of the slave unit always translates along a virtual axis parallel to the longitudinal axis of
(Continued)

the guided master link in the vicinity of the remote manipulation when the mechanical teleoperated device is operated.

11 Claims, 13 Drawing Sheets

(51) Int. Cl.
*A61B 17/00* (2006.01)
*A61B 17/29* (2006.01)
*B25J 3/02* (2006.01)
*B25J 13/02* (2006.01)
*A61B 34/37* (2016.01)
*A61B 34/00* (2016.01)
*A61B 90/50* (2016.01)
*A61B 90/00* (2016.01)

(52) U.S. Cl.
CPC .............. *A61B 34/37* (2016.02); *A61B 34/70* (2016.02); *A61B 34/71* (2016.02); *A61B 34/74* (2016.02); *A61B 34/77* (2016.02); *B25J 3/02* (2013.01); *B25J 13/02* (2013.01); *A61B 2017/291* (2013.01); *A61B 2034/715* (2016.02); *A61B 2090/372* (2016.02); *A61B 2090/506* (2016.02)

(58) Field of Classification Search
USPC ................ 700/3; 606/130, 205, 209; 702/12
See application file for complete search history.

(56) References Cited

U.S. PATENT DOCUMENTS

| | | | | |
|---|---|---|---|---|
| 5,784,542 A | * | 7/1998 | Ohm | B25J 3/04 700/247 |
| 6,026,701 A | | 2/2000 | Reboulet | |
| 8,992,564 B2 | * | 3/2015 | Jaspers | A61B 19/22 606/1 |
| 2003/0155747 A1 | | 8/2003 | Bridges | |
| 2006/0043698 A1 | | 3/2006 | Bridges | |
| 2006/0178559 A1 | * | 8/2006 | Kumar | A61B 34/30 600/109 |
| 2007/0137371 A1 | * | 6/2007 | Devengenzo | A61B 19/2203 74/490.01 |
| 2010/0011900 A1 | * | 1/2010 | Burbank | A61B 34/71 74/490.06 |
| 2010/0121347 A1 | | 5/2010 | Jaspers | |
| 2012/0132018 A1 | | 5/2012 | Tang et al. | |
| 2012/0209292 A1 | | 8/2012 | Devengenzo et al. | |

FOREIGN PATENT DOCUMENTS

| | | |
|---|---|---|
| WO | WO-8200611 A1 | 3/1982 |
| WO | WO 97/43942 | 11/1997 |
| WO | WO 98/25666 | 6/1998 |
| WO | WO-03086219 | 10/2003 |
| WO | WO 2008/130235 | 10/2008 |
| WO | WO-2010130817 A1 | 11/2010 |
| WO | WO 2012/049623 | 4/2012 |

OTHER PUBLICATIONS

European Application No. 12767107.1 filed Dec. 10, 2013.
Indian Application No. 887/DELNP72014 filed Feb. 6, 2014.
PCT Application No. PCT/IB2012/053786 filed Jul. 25, 2012.
Swiss Search Report dated Jun. 4, 2012.
International Search Report PCT/ISA/210 for PCT/IB2012/053786 dated Jan. 18, 2013.

* cited by examiner

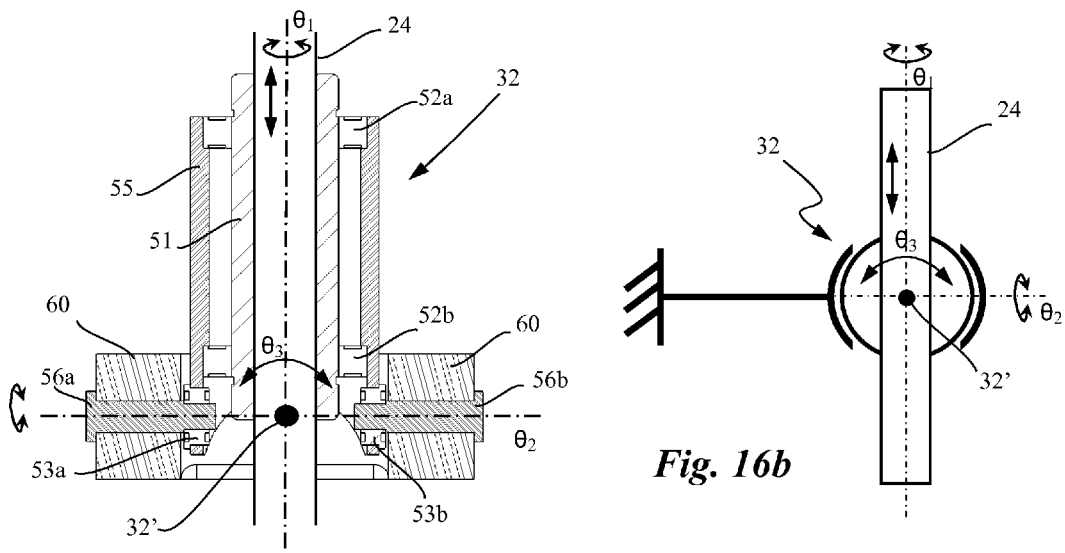
*Fig. 16a*  *Fig. 16b*
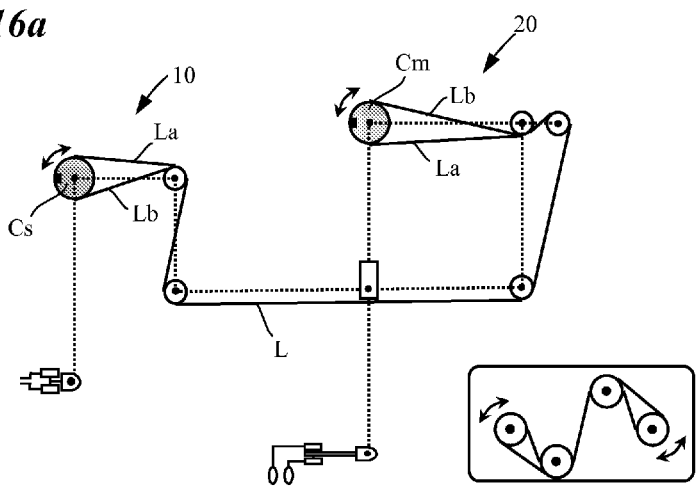
*Fig. 17*
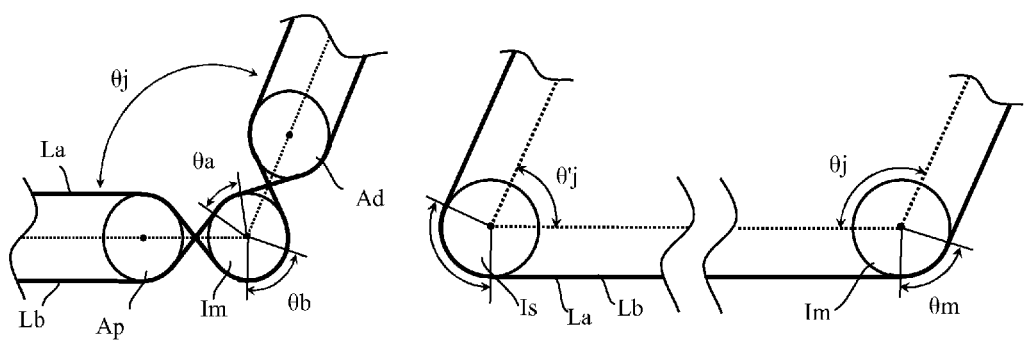
*Fig. 18*  *Fig. 19*

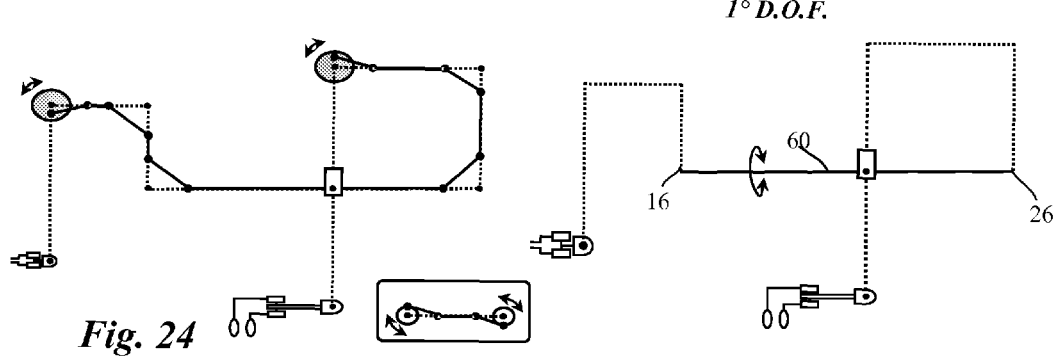
Fig. 24
Fig. 25
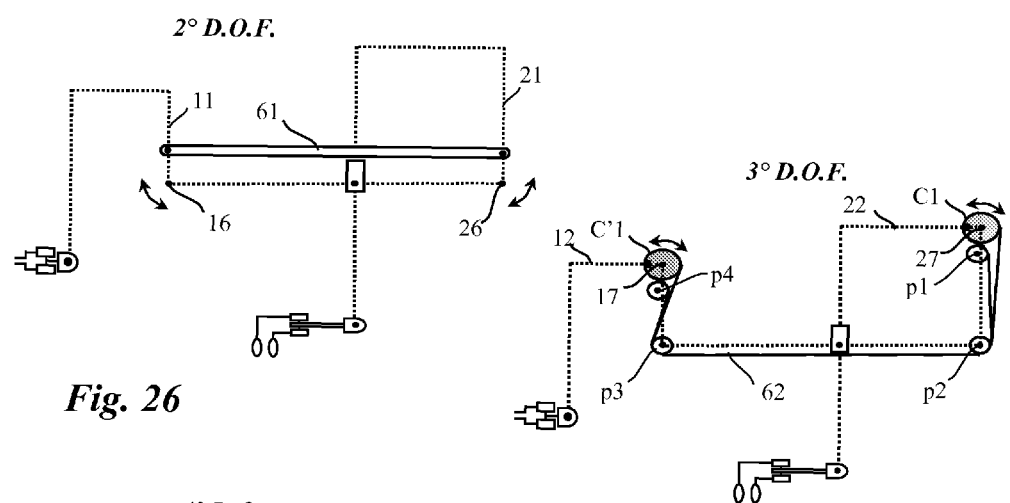
Fig. 26
Fig. 27
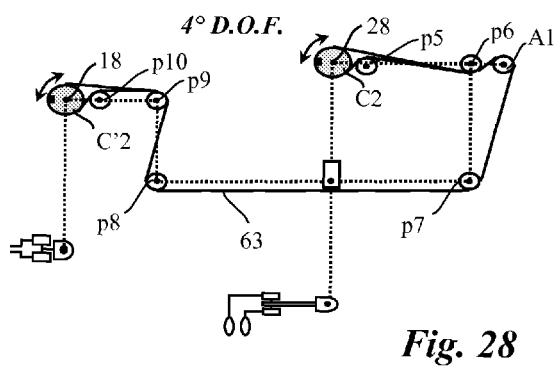
Fig. 28

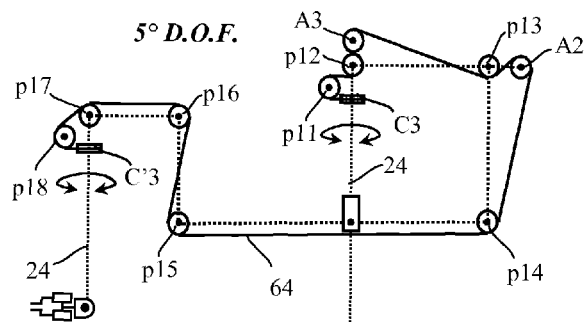
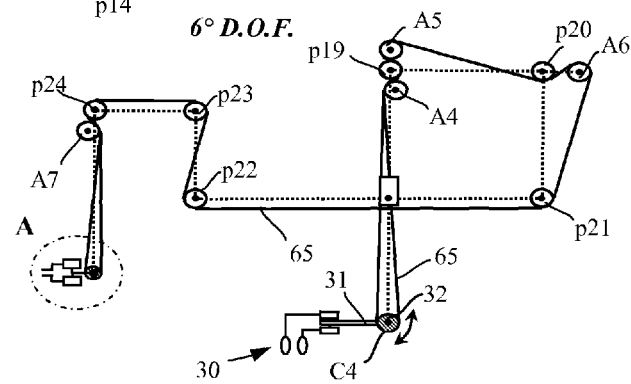
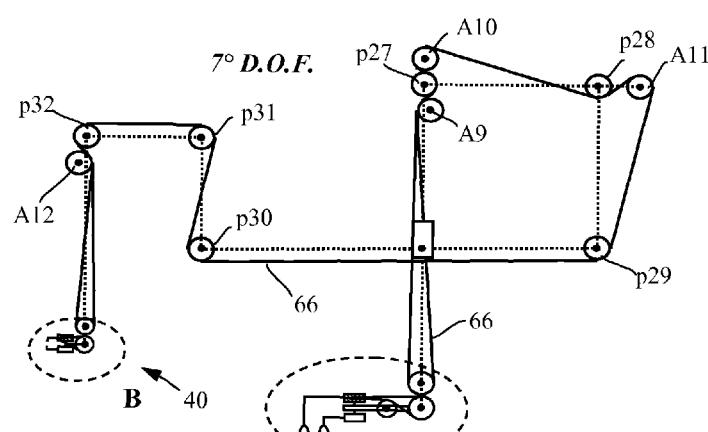
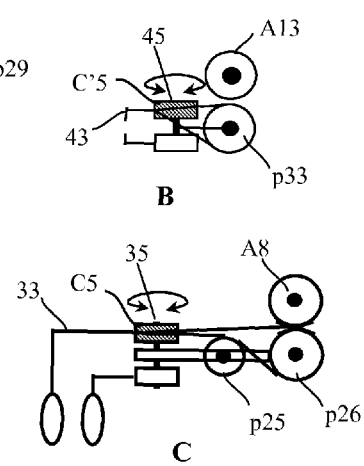
Fig. 29
Fig. 30
Fig. 31

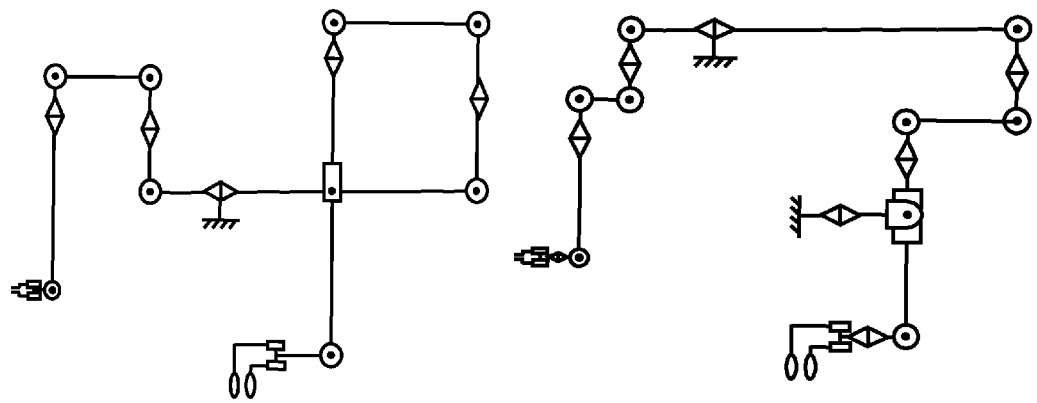
*Fig. 34*        *Fig. 35*
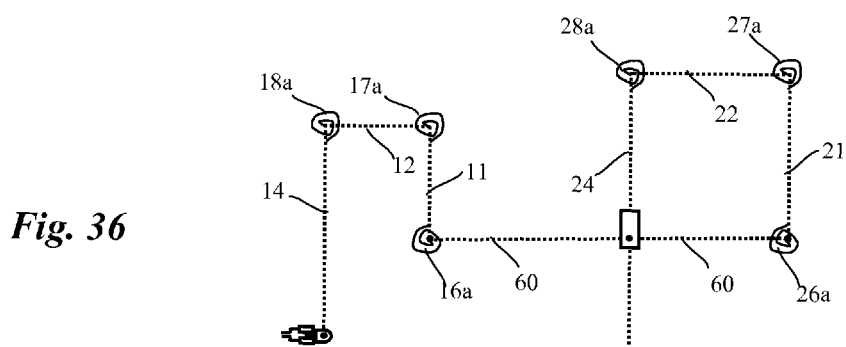
*Fig. 36*
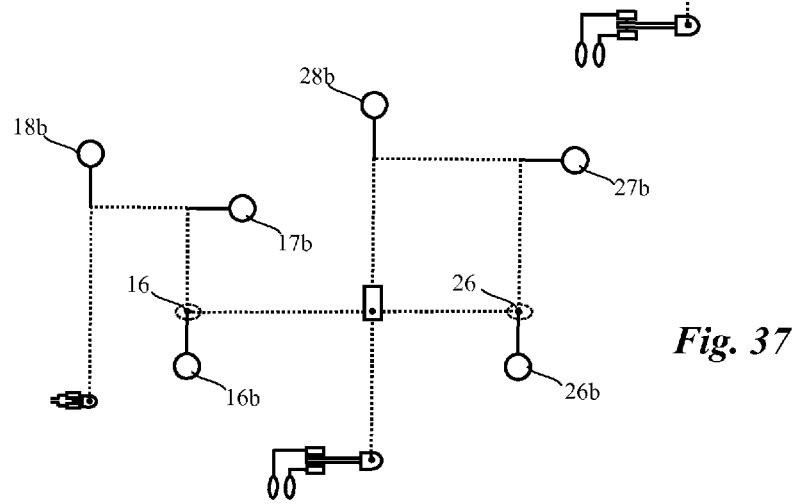
*Fig. 37*

MECHANICAL TELEOPERATED DEVICE FOR REMOTE MANIPULATION

This application is the national phase under 35 U.S.C. §371 of PCT International Application No. PCT/IB2012/053786 which has an International filing date of Jul. 25, 2012, which designated the United States of America and which claims priority to Swiss patent application number 00702/12 filed May 18, 2012 and U.S. Application No. 61/511,994, filed Jul. 27, 2011, the entire contents of each of which are hereby incorporated herein by reference.

FIELD OF THE INVENTION

The present invention relates to the field of remotely actuated mechanical systems and more particularly to a mechanical teleoperated device for remote manipulation for use primarily in minimally invasive surgical procedures, using small size access incisions into the patient body. This device is also adapted for any suitable remote actuated application requiring a dexterous manipulation with high stiffness, precision and quality force feedback such as assembly manipulation, manipulation in narrow places, manipulation in dangerous or difficult environments, and manipulation in contaminated or clean environments.

BACKGROUND OF THE INVENTION

Open Surgery is still the standard technique for most surgical procedures. It has been used by the medical community for several decades and consists of performing the surgical tasks by a long incision in the abdomen, through which traditional surgical tools are inserted. However, due to the long incision, this approach is extremely invasive for the patients, resulting in substantial blood loss during the surgery and long and painful recovery periods at the hospital.

In order to reduce the invasiveness of open surgery, laparoscopy, a minimally invasive technique, was developed. Instead of a single long incision, four to five small incisions are made in the patient through which long and thin surgical instruments and endoscopic cameras are inserted. Because of the low invasiveness, this technique reduces blood loss and shortens hospital stays and pain. When performed by experienced surgeons, this technique can attain clinical outcomes similar to Open Surgery. However, despite the above-mentioned advantages, laparoscopy requires extremely advanced surgeon skills to manipulate the rigid and long instrumentation. The entry incision acts as a point of rotation, decreasing the freedom for positioning and orientating the instruments inside the patient. The movements of the surgeon's hand about this incision are inverted and scaled-up relative to the instrument tip ("fulcrum effect"), which removes dexterity, sensibility and magnifies the tremors of the surgeon hands. In addition, these long and straight instruments force the surgeons to work in a uncomfortable posture for hands, arms and body, which can be tremendously tiring during several hours of operation. Therefore, due to these drawbacks of the laparoscopic instrumentation, these minimally invasive techniques are mainly limited to use in simple surgeries, while only a small minority of surgeons is able to use them in complex procedures.

To overcome these limitations, surgical robotic systems were developed to provide an easier-to-use approach to complex minimally invasive surgeries. By means of a computerized robotic interface, these systems enable the performance of a remote laparoscopy where the surgeon sits at a console manipulating two master manipulators to perform the operation through several small incisions. Like laparoscopy, the robotic approach is also minimally invasive, bringing several advantages over open surgery in terms of pain, blood loss, and recovery time. In addition, it also offers better ergonomy for the surgeon compared to open and laparoscopic techniques. However, although being technically easier, Robotic Surgery brings several negative aspects. A major disadvantage of these systems is related with the extremely high complexity of the existing robotic devices, which are composed by complex mechatronic systems, leading to huge costs of acquisition and maintenance, which are not affordable for the majority of surgical departments worldwide. Another drawback of these systems comes from the fact that current surgical robots are voluminous, competing for precious space within the operating room environment and significantly increasing preparation time. Access to the patient is thus impaired, which, together with the lack of force-feedback, raises safety concerns.

WO9743942, WO9825666 and US2010011900 disclose a robotic tele-operated surgical instrument, designed to replicate surgeons' hand movements inside the patient's body. By means of a computerized, robotic interface, it enables the performance of a remote Laparoscopy where the surgeon sits at a console manipulating two joysticks to perform the operation through several small incisions. However, this system does not have autonomy or artificial intelligence, being essentially a sophisticated tool fully controlled by the surgeon. The control commands are transmitted between the robotic master and robotic slave by a complex computer-controlled mechatronic system, which is extremely costly to produce and maintain and difficult to use by the hospital staff.

WO 2008130235 discloses a less complex mechanical manipulator for an instrument for minimally invasive surgery, having at a proximal end a handle for operating the instrument connected at a distal end of the manipulator. A parallelogram construction is provided between the proximal end and the distal end for guaranteeing an unambiguous position relationship between the handle and the instrument. This parallelogram construction is coupled with a system of bars for controlling the position of the parallelogram construction. The bars of the system are connected to the parallelogram construction as well as to each other by means of cardan joints.

The parallelogram constraint imposed by this mechanical manipulator renders difficult to obtain a scaled ratio other than 1:1 between the amplitude of the movements applied on the handle of this manipulator and the amplitude of the movements reproduced by the instrument connected at the distal end of the manipulator. This reduces the precision of the manipulator which is at the utmost importance for surgical intervention.

Furthermore, the handle of the manipulator of WO 2008130235 is connected to an extended arm which is slidably mounted along a guiding element. This ensures that the extended arm always translates along its longitudinal axis so that the instrument always translates along a virtual axis parallel to the longitudinal axis of said extended arm. The guiding element is eccentrically mounted rotatably on a supporting structure which causes the instrument to rotate around a stationary single point at a certain distance of this point which is not adequate when constraints are imposed by an incision realized on a patient. In addition, due to the high inertia of the rigid elements of the parallelogram construction, this mechanical manipulator provides poor haptic transparency.

Several other mechanical systems have been developed for remote manipulation in radioactive environments and are disclosed in several documents, such as US2846084. However, although the system disclosed in this document comprises a master-slave architecture, its dimensions, weight and kinematics are not suitable for minimally invasive surgical applications.

Accordingly, an aim of the present invention is to provide a mechanical teleoperated device preferably for minimally invasive surgical procedures capable of manipulating surgical instruments with higher precision, increased haptic transparency and which overcomes the aforementioned drawbacks of the prior art.

Another aim of the present invention is to provide a mechanical teleoperated device which can be easily adapted to be used for other forms of minimally invasive surgery as well as open surgery or procedures on MRi environments.

SUMMARY OF THE INVENTION

Theses aims and other advantages are achieved by a mechanical teleoperated device for remote manipulation, designed to naturally replicate the operator's hand movements in the vicinity where manipulations must occur. This mechanical teleoperated device comprises: i) a slave manipulator (referred hereafter as a "slave unit") having a number of slave links interconnected by a plurality of slave joints; ii) an end-effector (instrument/tool or a gripper/holder) connected to the distal end of the slave unit; iii) a master maniplulator (referred hereafter as a "master unit") having a corresponding number of master links interconnected by a plurality of master joints; and iv) a handle for operating the mechanical teleoperated device. The mechanical teleoperated device can also be described by considering the end-effector to be part of the slave unit and the handle to be part of the master unit. In a broader sense, the links and joints composing the end-effector can be considered distal slave links and joints, while the links and joints composing the handle can be considered distal master links and joints. The end-effector might be adapted to be releasable from the proximal part of the slave unit.

The mechanical teleoperated device further comprises first mechanical transmission means arranged to kinematically connect the slave unit with the master unit such that the movement (angle of joint) applied on each master joint of the master unit is reproduced by the corresponding slave joint of the slave unit at a predetermined scale ratio, which can advantageously by in the order of 2:1 or 3:1, if each master link is respectively two or three times longer than the corresponding slave link. A scaling down ration of this order of magnitude can significantly improve the precision of the device. In addition, second mechanical transmission means are arranged to kinematically connect the tool or the end-effector with the handle such that the movements applied on the handle is reproduced by the end-effector a predetermined scaled ratio The mechanical teleoperated device also comprises mechanical constraint means which are configured to ensure that one master link of said master unit is guided or constrained to move along its longitudinal axis so that the corresponding slave link of the slave unit always translates along a virtual axis parallel to the longitudinal axis of said guided master link in the vicinity of the remote manipulation when the mechanical teleoperated device is operated.

According to the invention, these mechanical constraint means are further configured to enable the guided master link of the master unit to rotate about its longitudinal axis, and about a second and a third axis. The longitudinal axis of the guided master link and the second and third axes always intersect each other at a stationary single point, independently of the orientation of said guided master link, enabling the corresponding slave link of the slave unit to rotate about its longitudinal axis, and about a fifth and a sixth virtual axis which are parallel respectively to the second and third axes about which the guided master link is rotatable. The longitudinal axis of the corresponding slave link and the fifth and sixth virtual axes always intersect each other at a virtual stationary single point in the vicinity of the remote manipulation (also referred as "remote center of motion").

According to one aspect of the invention, the kinematic model of the chain formed by the plurality of articulated slave and corresponding slave joints of the slave unit is identical to the kinematic model of the chain formed by the plurality of articulated master links and corresponding master joints of the master unit.

According to another aspect of the invention, the first mechanical transmission means are configured such that each slave link of the slave unit and the corresponding master link of the master unit move substantially parallel to each other when the mechanical teleoperated device is operated.

According to another aspect of the invention, the end-effector comprises a plurality of at least two and preferably three articulated end-effector links interconnected by end-effector joints. The handle comprises a corresponding plurality of at least two and preferably three corresponding articulated handle links interconnected by handle joints.

According to another aspect of the invention, the kinematic model of the chain formed by the plurality of articulated end-effector links and the corresponding end-effector joints of the end-effector is identical to the kinematic model of the chain formed by the plurality of the articulated handle links and corresponding handle joints of the handle.

According to another aspect of the invention, said second mechanical transmission means are configured such that each articulated end-effector link and the corresponding articulated handle link move substantially parallel to each other when said mechanical teleoperated device is operated.

According to another aspect of the invention, the amplitude of the movement applied on each handle link of the handle is reproduced by the corresponding end-effector link of the end-effector at a first predetermined scale ratio which corresponds to the ratio between the length of each end-effector link and the length of the corresponding handle link.

According to another aspect of the invention, the amplitude of the movement of each master link of the master unit, when the mechanical teleoperated device is operated, is reproduced by the corresponding slave link of the slave unit at a second predetermined scale ratio which corresponds to the ratio between the length of each slave link and the length of the corresponding master link.

According to another aspect of the invention, the second and third axes, about which the guided master link is rotatable, are substantially perpendicular to each other so that the fifth and sixth virtual axes, about which the corresponding slave link is rotatable, are substantially perpendicular to each other.

According to another aspect of the invention, the slave and master units are connected together by a connecting link adapted to pivot about its longitudinal axis which is aligned with said stationary point and said corresponding virtual stationary point.

According to another aspect of the invention, the master unit comprises at least three links arranged to form substantially a polygon construction of at least four sides with the connecting link, wherein one of said second and third axes is perpendicular to a plane defined by the polygon construction.

According to another aspect of the invention, the guided master link of the master unit is oriented to extend through an aperture of the connecting link of the master unit in a direction to a reference ground plane on which said mechanical teleoperated device rests when in operation. The handle of the mechanical teleoperated device is connected to one extremity of said guided master link of the master unit to be actuated below said connecting link.

According to another aspect of the invention, the slave and master units are separated apart from each other by a predetermined distance. A part of the first mechanical transmission means is arranged along the predetermined distance in order to kinematically connect each slave joint of the slave unit with the corresponding master joint of the master unit. A part of the second mechanical transmission means is arranged along said predetermined distance in order to kinematically connect each joint of the end-effector with the corresponding joint of the handle.

According to another aspect of the invention, the master unit comprises a first master link connected to a first master joint at one extremity and extending upwardly and substantially perpendicularly with reference to the connecting link, when the mechanical teleoperated device is in a neutral position, to be connected to a second master joint at its other extremity; a second master link connected to the second master joint at one extremity and extending to be connected to a third master joint at its other extremity; a third master link connected to the third master joint at one extremity and to a fourth master joint at its other extremity. One extremity of the guided master link is connected to the fourth master joint such that the guided master link is axially rotatable about its longitudinal axis and extends downwardly across the connecting link through the mechanical constraint means.

According to another aspect of the invention, the handle of the teleoperated device comprises a first handle link which is connected to one extremity of said guided master link through a first handle joint. The axis of rotation of the first handle link is substantially perpendicular and intersecting to the longitudinal axis of the guided master link. The handle further comprises a second and a third handle link connected to the first handle link trough respectively a second and a third handle joint coaxially mounted to each other.

According to another aspect of the invention, the slave unit comprises a first slave joint connected to one extremity of the connecting link; a first slave link connected to the first slave joint at one extremity and extending upwardly and substantially perpendicularly with reference to the connecting link, when the teleoperated device is in a neutral position, to be connected to a second slave joint at its other extremity; a second slave link connected to the second slave joint at one extremity and extending to be connected to a third slave joint at its other extremity; a third slave link connected to the third slave joint at one extremity and to a fourth slave joint at its other extremity. The fourth slave joint is coupled with a fourth slave link so that said fourth slave link is axially rotatable about its longitudinal axis and extends substantially downwardly.

According to another aspect of the invention, the end-effector comprises a first end-effector link which is connected at one extremity of said fourth slave link through a first end-effector joint. The axis of rotation of the first end-effector link is substantially perpendicular to and intersecting the longitudinal axis of the fourth slave link. The end-effector further comprises a second and a third end-effector link connected to the first end-effector link trough respectively a second and a third end-effector joint coaxially mounted to each other.

According to another aspect of the invention, the first mechanical transmission means comprise: (i) a first mechanical transmission arranged to kinematically connect the a proximal master joint of the master unit to a proximal slave joint of the slave unit so that said master and slave units are rotatable together along the longitudinal axis of the connecting link; (ii) a second mechanical transmission arranged to kinematically connect the first master joint of the master unit to the first slave joint of the slave unit so that the movement applied on the first master joint of the master unit is reproduced by the first slave joint of the slave unit; (iii) a third mechanical transmission arranged to kinematically connect the second master joint of the master unit to the second slave joint of the slave unit so that the movement applied on the second master joint of the master unit is reproduced by the second slave joint of the slave unit; (iv) a fourth mechanical transmission arranged to kinematically connect the third master joint of the master unit to the third master joint of the slave unit so that the movement applied on the third master joint of the master unit is reproduced by the third slave joint of the slave unit; and (v) a fifth mechanical transmission arranged to kinematically connect the fourth master joint of the master unit to the fourth master joint of the slave unit so that the movement applied on the fourth master joint of the master unit is reproduced by the fourth slave joint of the slave unit.

According to another aspect of the invention, the second mechanical transmission means comprise: (vi) a sixth mechanical transmission arranged to kinematically connect the first handle joint of the handle to the first end-effector joint of the end-effector; (vii) a seventh mechanical transmission arranged to kinematically connect the second handle joint of the handle to the second end-effector joint of the end-effector; and (viii) a eight mechanical transmission arranged to kinematically connect the third handle joint of the handle to the third end-effector joint of the end-effector.

According to another aspect of the invention, a plurality of slave and master joints of respective slave and master units are actuated by pulleys and/or pinions which are fixed to different slave and master links of the teleoperated device. Mechanical transmission means comprise one transmission loop or a plurality of transmission loops of flexible and/or rigid elements mounted to transmit the motion from each of the plurality of master pulleys and/or pinions of the master unit to the corresponding slave pulleys or pinions of the slave unit.

According to an optional aspect of the invention, the teleoperated device comprises gravity-compensating means in the form of springs that are mounted on a plurality of master and slave joints or in the form of counterweights connected to a plurality of master and slave links.

According to another optional aspect of the invention, the teleoperated device comprises locking means to lock said device in a stationary configuration when the surgeon is not holding the handle and when the device is in an active position.

Another aspect of the invention is to provide a mechanical manipulator comprising at least two mechanical teleoperated devices as defined above and mounted preferably parallel to each other on a station. Each mechanical teleoperated device is configured to be operated independently from the other.

According to another aspect of the invention, a third mechanical teleoperated device, as defined above is mounted on the station and is configured to be operated independently from the two other mechanical teleoperated device. The distal end of the third mechanical teleoperated device is adapted to receive a camera or an assisting tool.

According to another aspect of the invention, each mechanical teleoperated device is mounted on an articulated supporting structure. Each supporting structure is connected to the station in a manner to be inclinable in the direction of said virtual stationary single point in the vicinity of the remote manipulation.

According to another aspect of the invention, each of the two or the three mechanical teleoperated devices is rotatably mounted on said station to be inclined along a side thereof to form preferably an angle between 60° and 90° with reference to a ground surface to enable said mechanical manipulator to be transported and compactly stored.

According to another aspect of the invention, the station is provided with a screen or with any other visual display configured to monitor the vicinity of the remote manipulation.

Finally, a last aspect of the invention is to provide a mechanical teleoperated surgical device, for minimally invasive surgical procedures, comprising the mechanical teleoperated device or the mechanical manipulator as defined above, wherein said surgical device comprises adjustment means to position said corresponding virtual stationary point, along and about which the corresponding link of the slave unit translates and rotates, in correspondence with a surgical incision realized on a patient.

This device is particularly well adapted for minimally invasive surgery. Like a robotic telemanipulator for surgery, this system does not have autonomy or artificial intelligence, being essentially a sophisticated tool completely controlled by the surgeon. However, this device uses a fully mechanical technology for the motion transmission as opposed to robotic systems which commands are transmitted between the master and slave by a computer-controlled mechatronic system. Without electronics, actuators and software, this device has also the potential to be more reliable, affordable to produce and easier to use, benefiting also from a more stable force-feedback to the surgeon.

The device uses a technology able to actuate systems with complex kinematics while being able to provide precision and high forces at very small scales. Mechanical transmission means as developed allow perfect kinematic matching between the corresponding joints of the slave and master units. This master-slave relationship allows the movement of any of the joints of master unit to be transmitted to the analogous joint of a slave unit. The low inertia of the links of the master and slave units and the low-friction of the mechanical transmission means provide backlash and ripple-free movements, which gives to the surgeon a realistic rendering of the forces at the distal instruments.

Due to its kinematic model, the system allows seven degrees of freedom to the surgical instruments, a range of motion even greater than the human wrist and fingers, providing great dexterity to the surgeon. Thanks to a remote-center-of-motion, the slave unit can be controlled by the master unit, while respecting the constraints imposed by the incision point realized on a patient, reducing trauma to the patient and improving cosmetic outcomes.

The design and performance specifications of this system were driven by surgical tasks requirements and its use can contribute to increase the performance of surgical procedures, increasing their reliability.

BRIEF DESCRIPTION OF FIGURES

The invention will be better understood thanks to the following detailed description of several embodiments of the invention with reference to the attached drawings, in which:

FIG. 16a shows a cross-sectional view of the mechanical constraint means of the mechanical teleoperated surgical device of FIG. 1;

FIG. 16b shows a schematic view of an alternative of mechanical constrain means;

FIG. 17 shows a schematic view of a single closed loop (cable) transmission between a general driven pulley of the slave unit and the corresponding driving pulley of the master unit of the mechanical teleoperated device;

FIG. 18 shows a schematic view of a cable rooting method to keep the closed loop with a constant length, at the joint level;

FIG. 19 shows a schematic view of another cable rooting method to keep the closed loop with a constant length, at equivalent master-slave joints level;

FIG. 24 shows a schematic view of a transmission using connecting rods between two general joints according to an even further embodiment of the invention;

FIGS. 25 to 32 show schematic views of the cabling topology for each of the eight degrees of freedom of the mechanical teleoperated device;

FIGS. 34 and 35 show different possible kinematic configurations of the mechanical teleoperated device according to different embodiments of the invention;

FIG. 36 shows a schematic view of the mechanical teleoperated device comprising torsion springs to reduce the effect of the gravity felt by the user on the handler, according to some embodiments of the invention, and FIG. 37 shows a variant of FIG. 36 where torsion springs are replaced by counterweights.

DETAILED DESCRIPTION OF THE INVENTION

Figure 1:
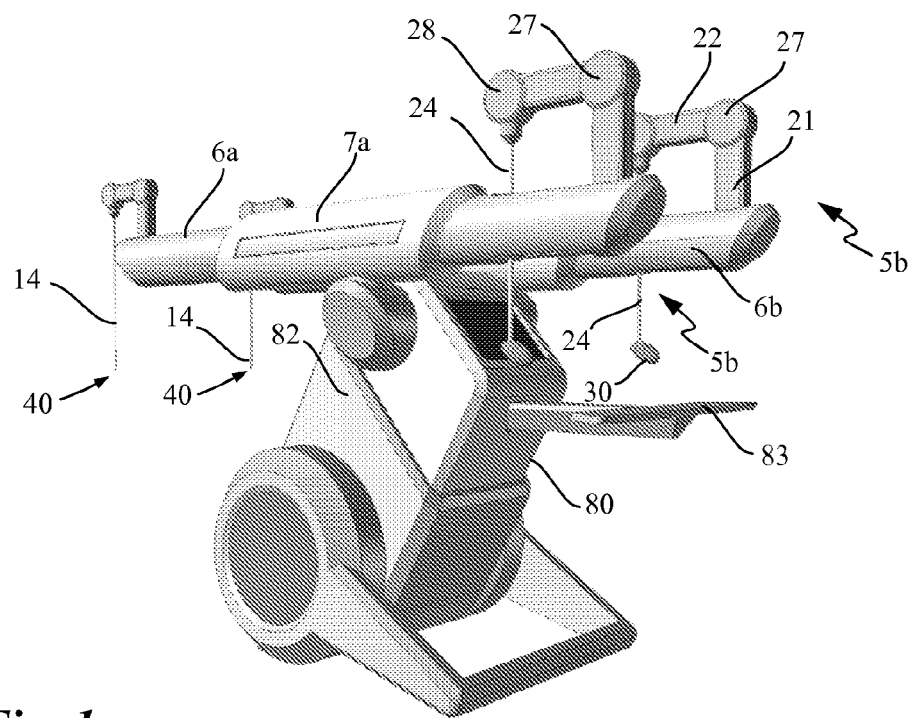
FIG. 1 shows a perspective view of a mechanical teleoperated surgical device according to a preferred embodiment of the invention.
Figure 2:
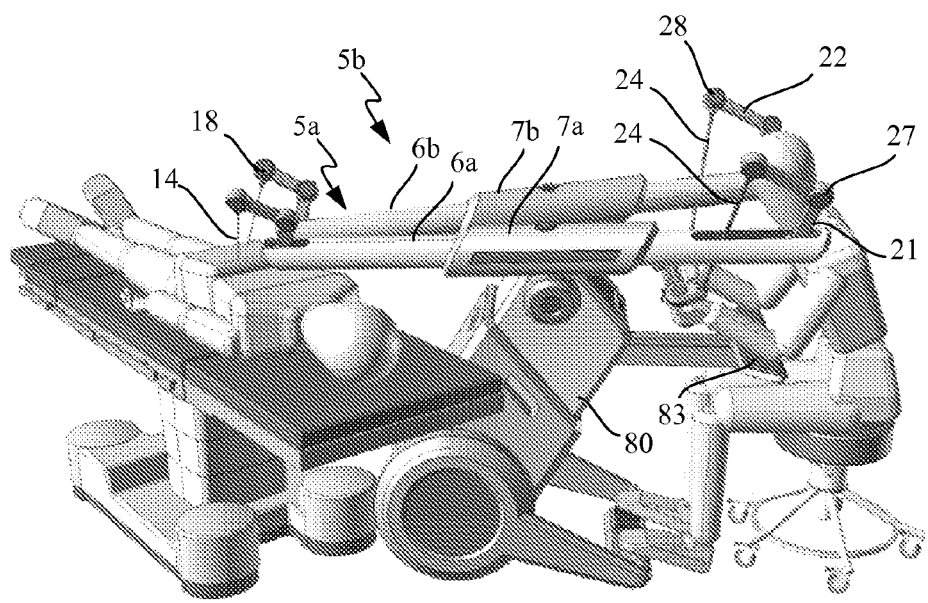
FIG. 2 shows a perspective view of the mechanical teleoperated surgical device of FIG. 1 operated by a surgeon during minimally invasive surgery.

A teleoperated surgical device for minimally invasive surgical procedures, constructed in accordance with a preferred embodiment of the present invention, is described herein, and is seen generally in FIGS. 1 and 2. This device includes preferably two identical mechanical teleoperated devices 5a, 5b configured to be operated independently from the other, and comprising each seven independent degrees of freedom. (in total, the system has eight degrees of freedom, but one of them is redundant). These two mechanical teleoperated devices 5a, 5b are respectively mounted partly inside a first and a second housing 6a, 6b which are substantially parallel to each other although the angle between them can be tuned.

Figure 3:
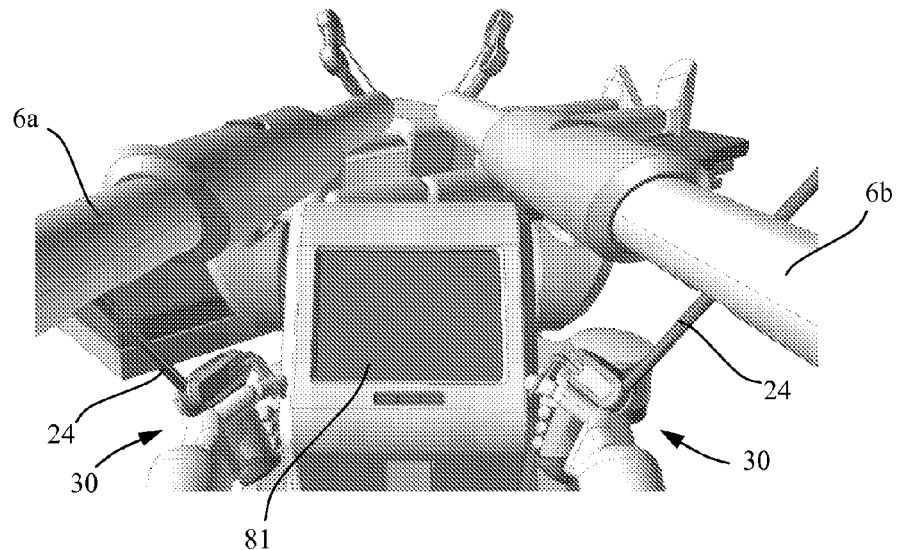
FIG. 3 shows the surgeon perspective when manipulating the mechanical teleoperated surgical device of FIG. 2.

With reference to FIGS. 2 and 3, the surgeon will perform the procedure directly manipulating two intuitive handles 30 in the proximal part of the teleoperated surgical device viewing the operation through an endoscopic vision system. The movements applied by the surgeon on the two handles 30 are replicated (scaled down or not) by two multi-articulated surgical tools 40 (FIG. 7) that reach the abdominal cavity of the patient through small incisions. Their movements can be seen through an external screen 81 as shown in FIG. 3. This teleoperated surgical device improves the ergonomic for surgeons, enabling them to position their hands in a natural orientation to each other, providing improved eye-hand coordination and intuitive manipulation with non-inversed movements. The comfort of the surgeons is also improved by an elbows support 83 as shown for example in FIG. 2.

Figure 4:
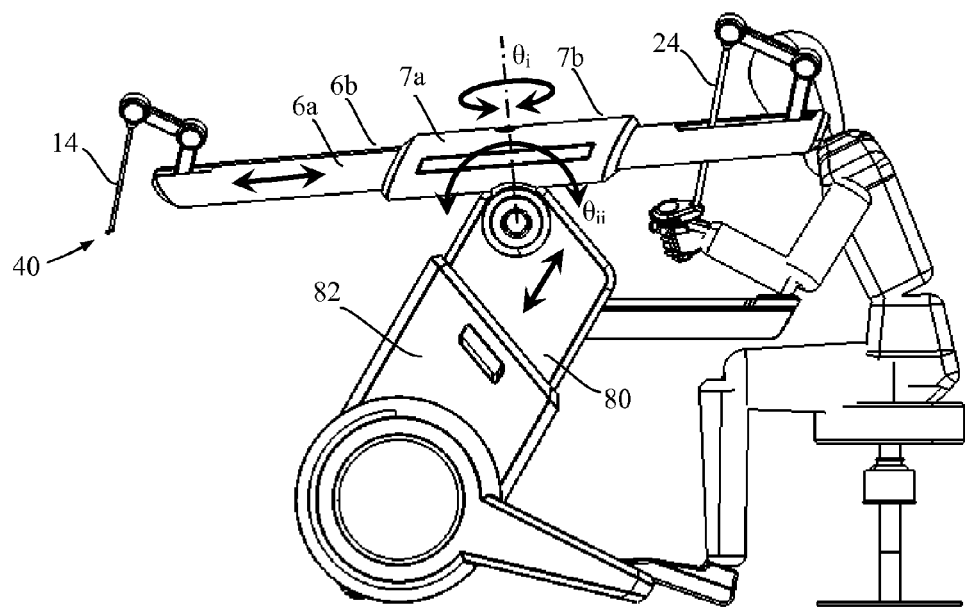
FIG. 4 shows adjustment means of the mechanical teleoperated surgical device for accurately positioning two distal tools in relation to the location of incision points realized on a patient.

Referring to FIG. 4, the first and second housing 6a, 6b of the two mechanical teleoperated devices 5a, 5b are slidably mounted inside respectively a first and a second tubular structure 7a, 7b to be linearly actuated along their respective structures. Each tubular structure 7a, 7b is articulated on a station 80 to rotate about a first axis $\theta_i$ and to tilt about a second axis $\theta_{ii}$. This station 80 is mounted inside a wheeled hollow base 82 and is adapted to rise in relation to this base 82. The combination of these movements allows to accurately position the incision points (the remote center of motion) and the two multi-articulated surgical tools 40 in the vicinity of the abdominal cavity of the patient.

Figure 5A:
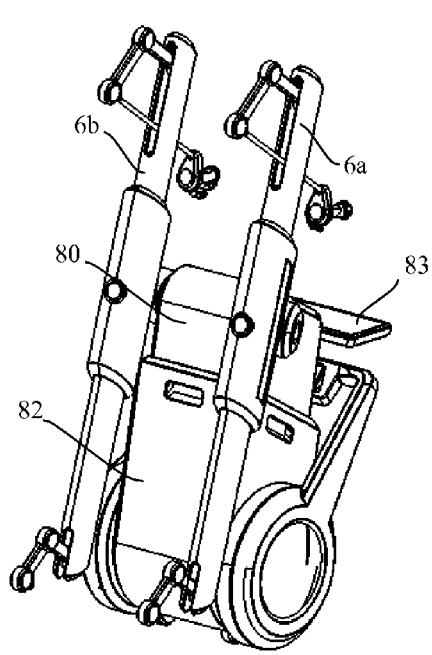
FIGS. 5a and 5b show respectively perspective front and back views of the mechanical teleoperated surgical device of FIG. 1 in a configuration to be easily transported and compactly stored.
Figure 5B:
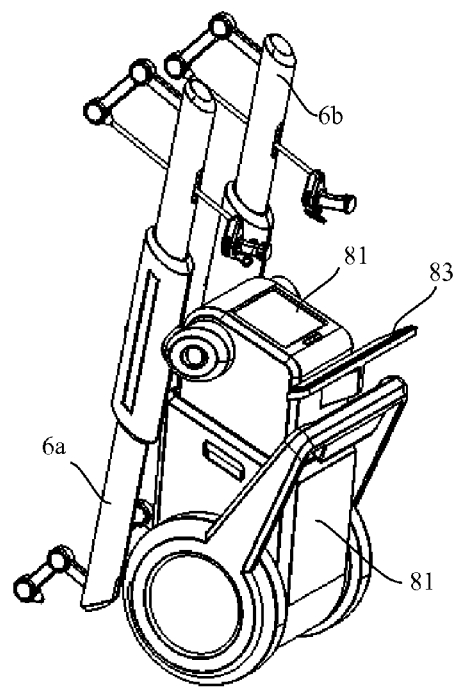

The two tubular structures 7a, 7b are further rotatably mounted on the station 80 such that the two mechanical teleoperated devices 5a, 5b can be advantageously inclined along a side of this station 80 to form preferably an angle between 60° and 90° and even more preferably between 70° and 80° with reference to a ground surface as shown in FIGS. 5a and 5b to enable the teleoperated surgical device to be easily transported and compactly stored.

One of the key features of the invention lies on the Master-Slave relationships configuration of each mechanical teleoperated devices 5a, 5b. A slave unit and a master unit are configured to work together, achieving a force reflecting teleoperation. Given that the two teleoperated devices 5a, 5b are structurally and functionally identical, the description hereafter will refer to one mechanical teleoperated device only.

Figure 8:
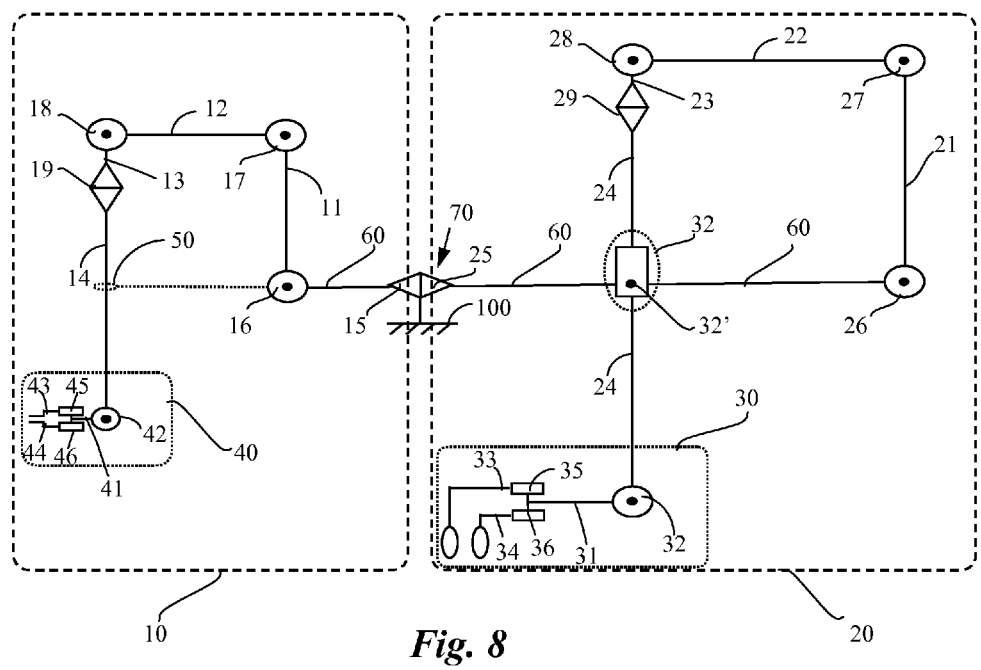
FIG. 8 shows a schematic view of the structural parts of the mechanical teleoperated surgical device of FIG. 1 in a Master-Slave relationship configuration.
Figure 10:
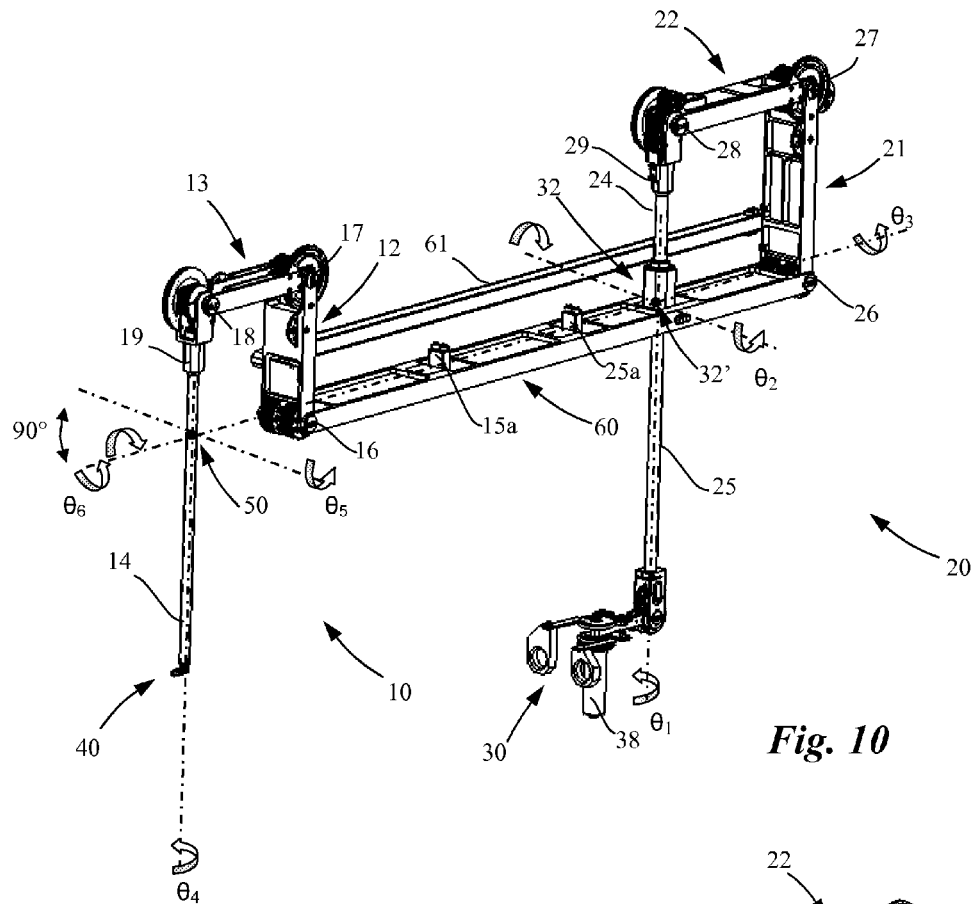
FIG. 10 shows a perspective view of the mechanical teleoperated surgical device of FIG. 1 in a neutral position.

FIG. 8 schematically illustrates the structural configuration of the teleoperated device according to the preferred embodiment of the invention. This device comprises a slave unit 10 and a master unit 20 connected to each other by a connecting link 60. This connecting link 60 comprises a joint 70 which connects the teleoperated device to a ground 100. This joint 70 can be decomposed in two master and slave joints 25, 15 which can respectively be considered as the first proximal joints of the master unit 20 and the slave unit 10. Referring to FIG. 10, the master and slave joints are materialized by two radial bearing 25a, 15a mounted on the connecting link 60 and adapted to receive a longitudinal shaft (not shown) such that the teleoperated device is rotatable about this shaft. In the case of decomposing joint 70 in joints 25 and 15, the segment of the of the connecting link 60 that goes from the slave joint 15 to the slave joint 16 is considered to be the proximal slave link and the segment of the of the connecting link 60 that goes from the master joint 25 to the master joint 26 is considered to be the proximal master link.

Figure 9:
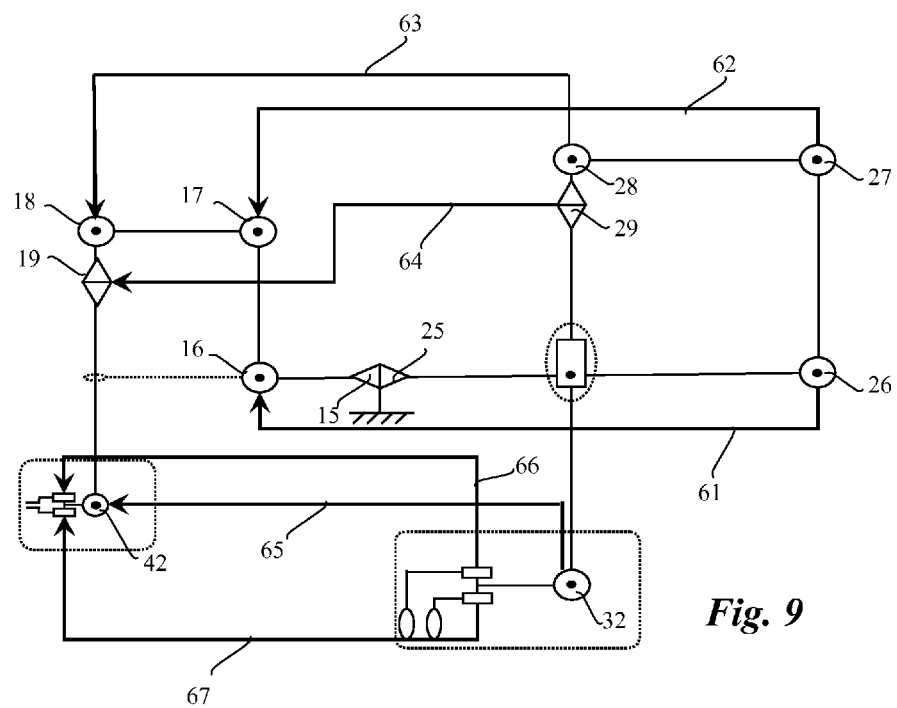
FIG. 9 shows a similar view of FIG. 8 with kinematical connections between the corresponding joints of the master and slave units.

The slave unit comprises a number of slave links 11, 12, 13, 14 interconnected by a plurality of slave joints 16, 17, 18, 19 whereas the master unit 20 comprises a corresponding number of master links 21, 22, 23, 24 interconnected by a plurality of master joints 26, 27, 28, 29. First mechanical transmission means 61, 62, 63, 64, as schematically shown in FIG. 9, comprise partly pulley-routed cables that are arranged to kinematically connect the slave unit 10 with the master unit 20 such that the movement (angle of the joint) applied on each master joint 26, 27, 28, 29 of the master unit 20 is reproduced by the corresponding slave joint 16, 17, 18, 19 of the slave unit 10. More particularly, the kinematic chain formed by the plurality of articulated slave links 11, 12, 13, 14 and corresponding slave joints 16, 17, 18, 19 of the slave unit 10, is identical to the kinematic chain formed by the plurality of articulated master links 21, 22, 23, 24 and corresponding master joints 26, 27, 28, 29 of the master unit 20.

Referring now more particularly to the structural parts of the master-slave units 10, 20 of FIG. 10, the master unit 20 comprises more specifically four master links 21, 22, 23, 24, that are interconnected to each other in a manner to form substantially a square construction with the connecting link 60 when the mechanical teleoperated device is in a neutral position. In this neutral position, the first master link 21 is pivotally connected at one extremity about a first shaft 26 and extends upwardly and substantially perpendicularly with reference to the connecting link 60 to be pivotally connected at the other extremity about a second shaft 27. The second master link 22 is pivotally connected at one extremity about this second shaft 27 and extends parallely to the first master link 21 to be pivotally connected at the other extremity about a third shaft 28. The third master link 23 as schematically shown in FIG. 8 is pivotally connected at one extremity about this third shaft 28 while one extremity of the fourth master link 24 is connected to the other extremity of the third master link 23 through an axial joint 29 such that this fourth master link 24 is axially rotatable about its longitudinal axis $\theta_1$ (FIG. 10) and extends downwardly through an aperture located on the connecting link 60. The handle 30 of the mechanical teleoperated device is connected to the other extremity of the fourth master link 24.

Still Referring to FIG. 10, the slave unit 10 comprises more specifically four slave links 11, 12, 13, 14 that are interconnected to each other in a manner to form, with the extension of the longitudinal axis $\theta_6$ of the connecting link 60, a substantially square construction when the teleoperated device is in a neutral position. The first slave link 11 is pivotally connected at one extremity about a fourth shaft 16 and extends upwardly and substantially perpendicularly with reference to the connecting link 60 to be pivotally connected at the other extremity about a fifth shaft 17. The second slave link 22 is pivotally connected at one extremity about the fifth shaft 17 and extends forwardly and parallely to the extension of the longitudinal axis $\theta_6$ of the connecting link 60 to be pivotally connected at the other extremity about a fifth shaft 18. The third slave link 13 as shown in FIG. 8 is pivotally connected at one extremity about the fifth shaft 18 while one extremity of the fourth slave link 14 is connected to the other extremity of the fourth slave link 14 through an axial joint 19 such that this fourth slave link 14 is axially rotatable about its longitudinal axis $\theta_4$ and extends downwardly.

Transmission 61 of the first mechanical transmission means 61, 62, 63, 64 is a rigid element (FIG. 10) to transmit the motion from the master joint 26 to the slave joint 16. Mechanical transmissions 62, 63, 64 of the first mechanical transmission means comprise several pulleys that are mounted to rotate about each of the first, second, third, fourth and fifth shafts 26, 27, 28, 16, 17, 18 of the master and slave units 10, 20 to partly kinematically connect these units 10, 20 together. More details about the configuration of these first mechanical transmission means will be provided further below.

In reference for example to FIG. 10, the multi-articulated end-effector 40 is connected at the distal end of the slave unit 10 whereas the handle 30 is connected at the distal end of the master unit 20 for operating the mechanical teleoperated device wherein the amplitude of the movements applied on the handle 30 by the surgeon is reproduced, at a predetermined scaled ratio, by end-effector 40 through second mechanical transmission means 65, 66, 67 (FIG. 9) which also comprise pulley-routed cables, as explained hereafter in more details. Ratios between the slave and the master units 10, 20 can be advantageously chosen according to the use. For instance, not only 1:1 can be used but also 2:1, 3:1 etc. in order to increase the precision of the telemanipulation and filter tremors of the user. Magnification ratios can also be used such as: 1:2, 1:3, etc.

With reference to FIG. 8, the handle 30 of the teleoperated device comprises a first handle link 31 which is connected to one extremity of the fourth master link 24 through a first handle joint 32. The axis of rotation of the first handle link 31 is substantially perpendicular to and intersecting the longitudinal axis $\theta_1$ of the fourth master link 24. The handle 30 further comprises a second and a third L-shaped link 33, 34 articulated at one extremity to the first handle link 31 trough respectively a second and a third handle joint 35, 36 whose axes are collinear with each other and substantially perpendicular to the axis of the first handle joint 32.

Figure 6:
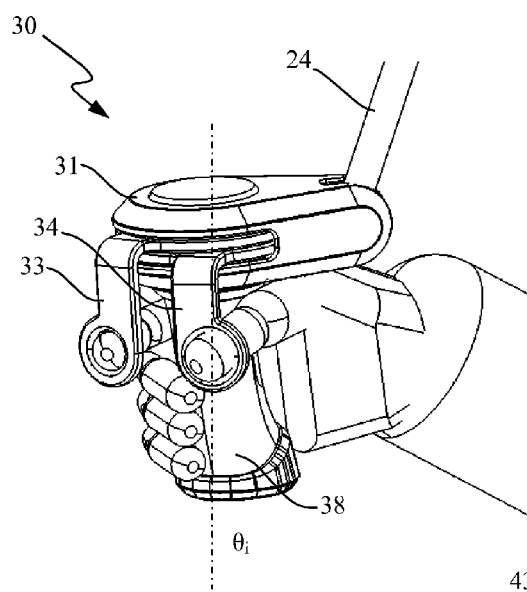
FIG. 6 shows a perspective view of the handle connected to the distal end of the master unit of the mechanical teleoperated surgical device.

Referring more particularly to FIG. 6, this handle 30 further comprises a holding stick 38 coaxially mounted to the second and third handle joint 35, 36 and configured to be hold by the palm of the hand and to freely rotate about its longitudinal axis $\theta_i$ which is collinear with the axis of the second and third handle joint 35, 36. The second and third L-shaped links 33, 34 comprise each at their other extremity an aperture 33a, 34a adapted to receive respectively the tips of the thumb and the index fingers.

Figure 7:
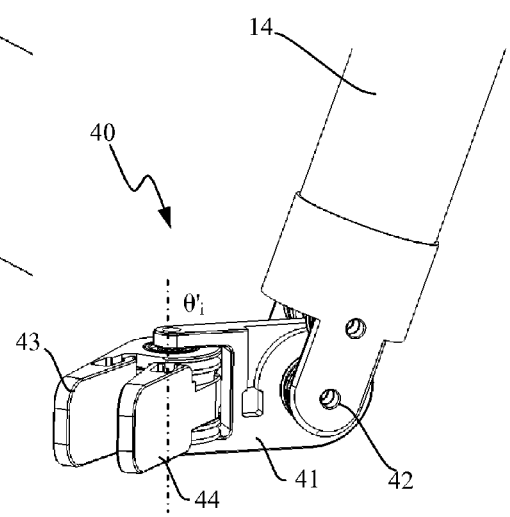
FIG. 7 shows a perspective view of the end-effector connected to the distal end of the slave unit of the mechanical teleoperated surgical device.

The end-effector 40 as shown in FIG. 7 is a surgical tool and comprises, in view of FIG. 8, a first tool link 41 which is connected to one extremity of the fourth slave link 14 through a first tool joint 42. The axis of rotation of the first tool link 41 is substantially perpendicular to and intersecting the longitudinal axis $\theta_4$ of the fourth slave link 15. In reference to FIG. 7, this surgical tool 40 further comprises two blades 43, 44 connected to the first tool link 41 trough respectively a second and a third tool joint 45, 66 coaxially mounted to each other. The handle 30 is kinematically connected to the surgical tool in a manner that the movement applied on the second and third handle link 33, 34 by the tips of the thumb and the index finger are reproduced by the two blades 43, 44.

The surgical tool 40 is interchangeable and can be of several types, such as scissors, scalpels, cutters, needle holders and other accessories to be connected to the distal end of salve unit 20. The surgical tool which enters the patient's body is bio-compatible and is reusable after sterilization. Disposal surgical tool can also be used.

Figure 11:
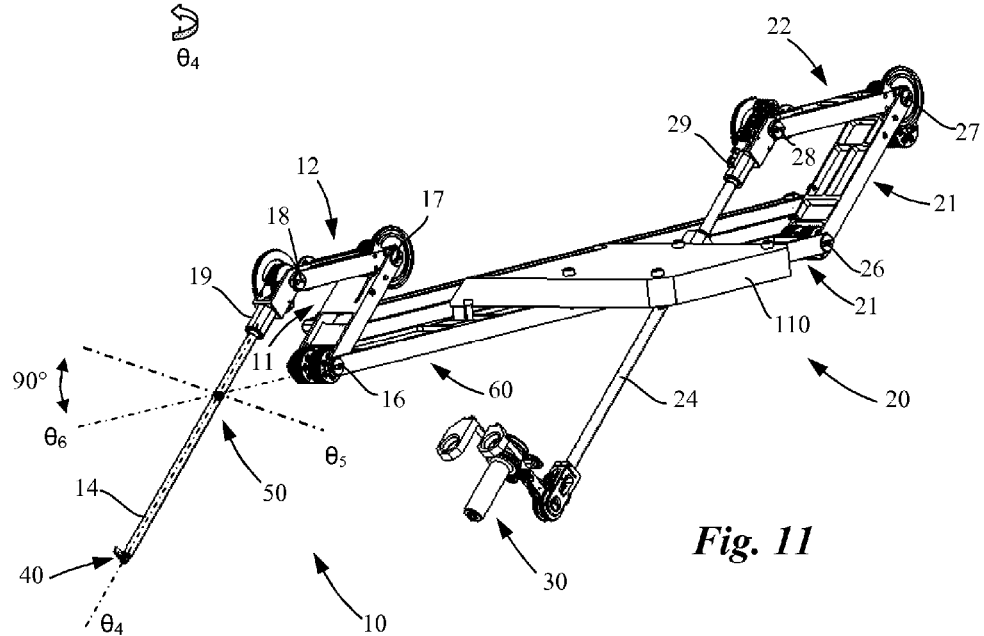
FIG. 11 shows a perspective view of the mechanical teleoperated surgical device of FIG. 1 in a first active position.
Figure 12:
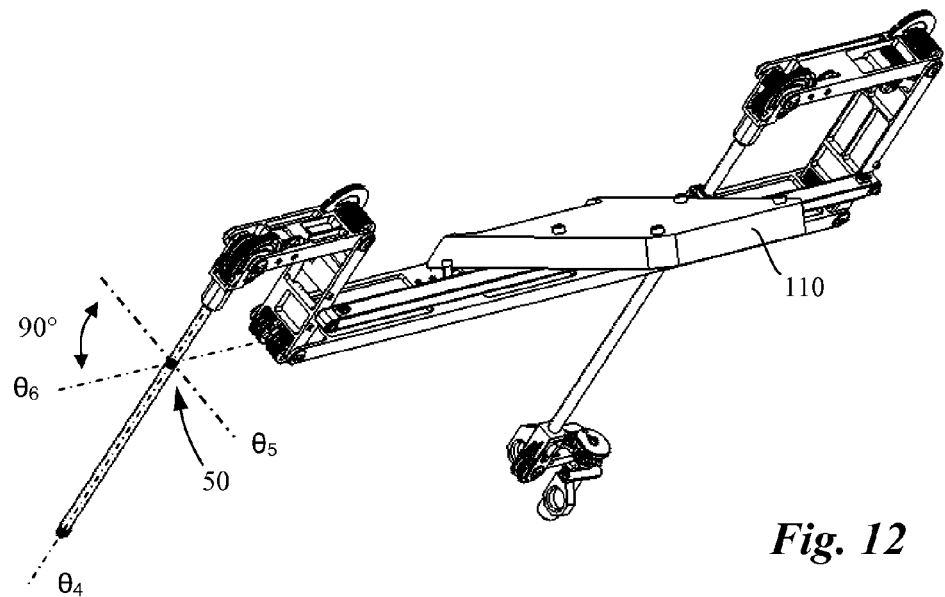
FIG. 12 shows a perspective view of the mechanical teleoperated surgical device of FIG. 1 in a second active position.
Figure 13:
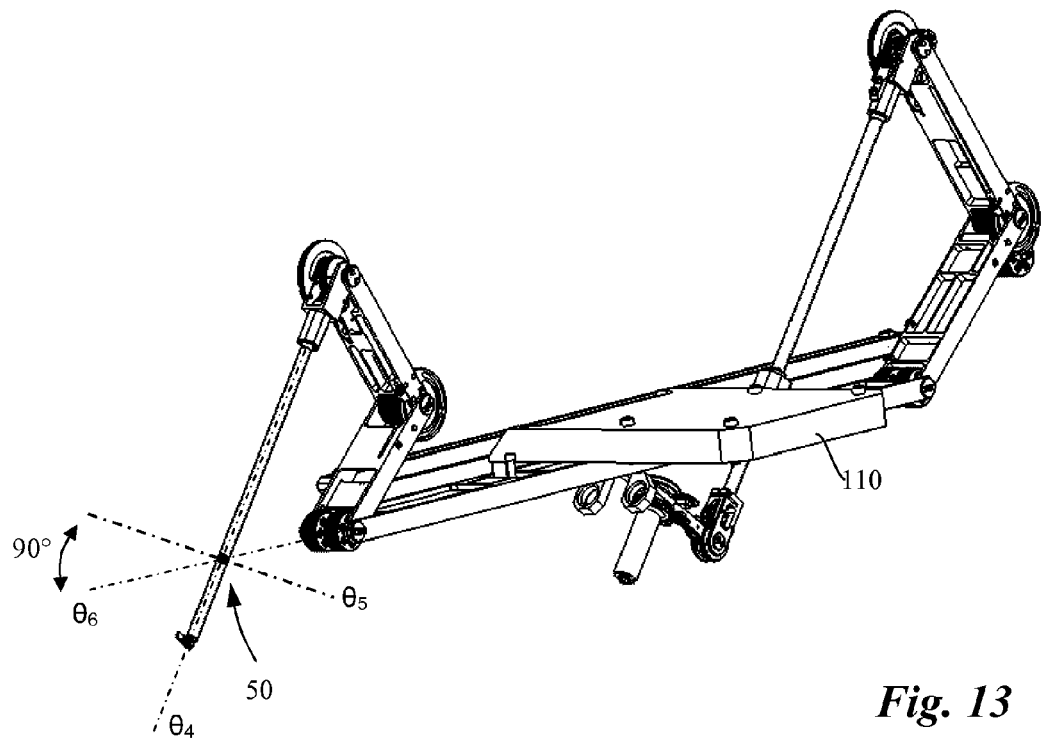
FIG. 13 shows a perspective view of the mechanical teleoperated surgical device of FIG. 1 in a third active position.
Figure 14:
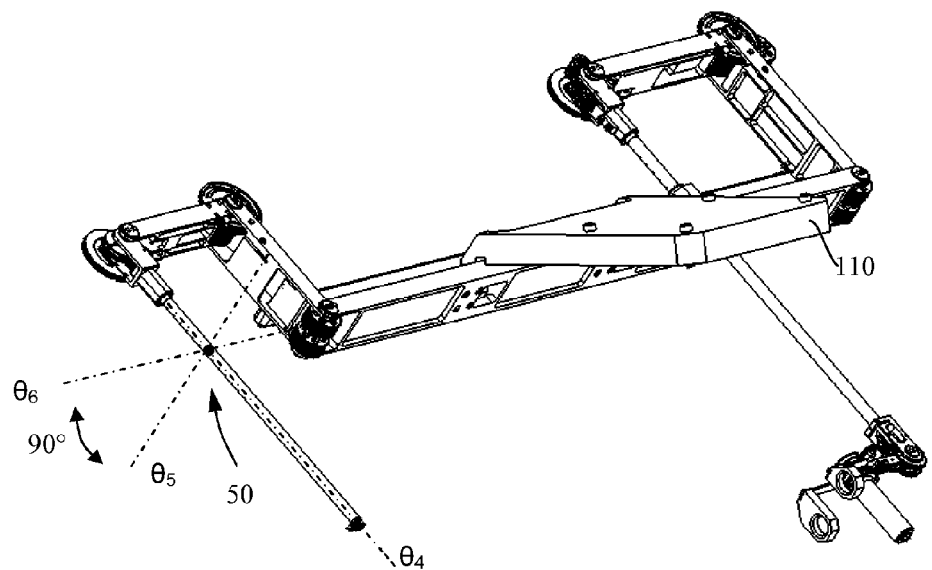
FIG. 14 shows a perspective view of the mechanical teleoperated surgical device of FIG. 1 in a fourth active position.
Figure 15:
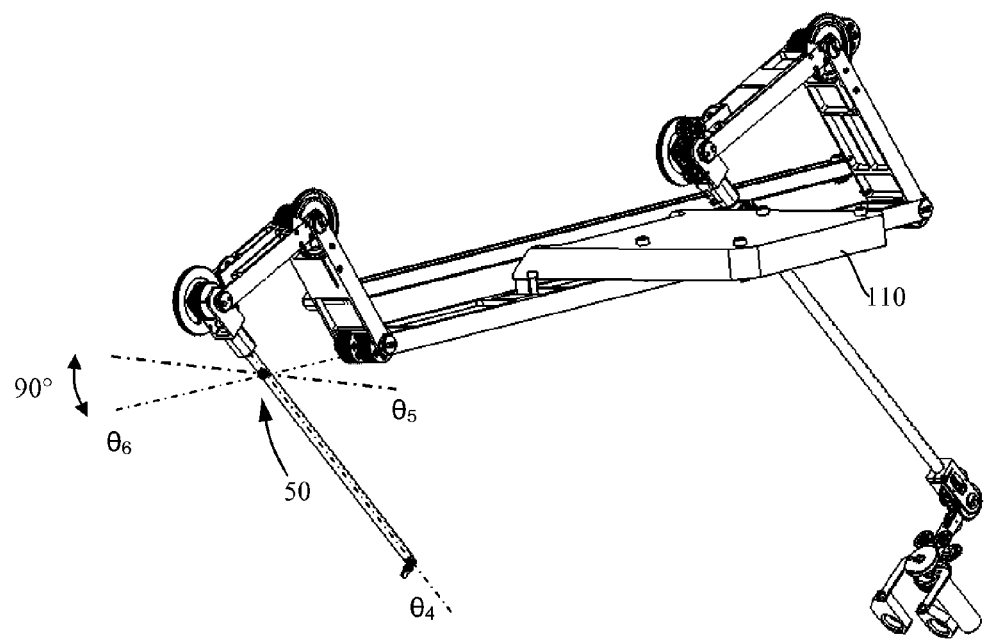
FIG. 15 shows a perspective view of the mechanical teleoperated surgical device of FIG. 1 in a fifth active position.

The movement applied on the handle 30, as shown for example in FIG. 11, forces the movement of the master joints 26, 27, 28, 29 of the master unit 20 which, by the direct mechanical transmission (FIG. 9) and the mechanical constraint means 32, drive the respective movement of the slave joints 16, 17, 18, 19 of the slave unit 10. As a result, the multi-articulated surgical tool 40 connected to the distal end of the slave unit 10 is moved in an equivalent movement of the handle 30 of the master unit 20. In a more general way, the direct connection between each of the master joints 26, 27, 28, 29 of the master unit 20 with the corresponding slave joint 16, 17, 18, 19 of the slave unit 10 forces each of the master links 21, 22, 23, 24 of the master unit 20 to be parallel to the corresponding slave link 11, 12, 13, 14 of the slave unit 10 independently of the active position of the teleoperated device as shown by FIGS. 11 to 15 which comprise each a reference base 110 to better illustrate the spatial orientation of the device.

Another key feature of the invention lies on mechanical constraint means 32 of the teleoperated device which are configured to constraint movements of the distal end of the slave unit 10 in correspondence with the constraints imposed by an incision realized on a patient. Referring to FIG. 10, the mechanical constraint means 32 are configured to ensure that, when the mechanical teleoperated device is in operation, the fourth master link 24 of the master unit 20 always translates along its longitudinal axis $\theta_1$ so that the corresponding link 14 of the slave unit 10 always translates along a virtual axis $\theta_4$ parallel to the longitudinal axis $\theta_1$ of this fourth master link 24 in the vicinity of the remote manipulation. These constraint means 32 are further configured to enable the fourth master link 24 of the master unit 20 to rotate about its longitudinal axis $\theta_1$, and about a second and a third axis $\theta_2$, $\theta_3$ that are perpendicular to each other. The longitudinal axis $\theta_1$ of the fourth master link 24 and said second and third axes $\theta_2$, $\theta_3$ always intersect each other at a stationary single point 32' (FIGS. 8, 10, 16a and 16b) independently of the orientation of the fourth master link 24. As illustrated by the different active positions of the teleoperated device in FIGS. 11 to 15, this configuration allows the corresponding link 14 of the slave unit 10 to rotate about its longitudinal axis $\theta_4$, and about a fifth and a sixth virtual axis $\theta_5$, $\theta_6$ that are perpendicular to each other. The longitudinal axis $\theta_4$ of the corresponding link 14 and the fifth and sixth virtual axes $\theta_5$, $\theta_6$ always intersect each other at a virtual stationary single point 50 (FIGS. 10 to 15) in the vicinity of the remote manipulation. During a minimally invasive surgical procedure, the virtual stationary point 50 is brought in coincidence with the surgical incision point, reducing trauma to the patient and improving cosmetic outcomes of the surgery.

As shown in FIG. 16a, the mechanical constraint means 32 comprise a linear bearing 51 through which the fourth master link 24 of the master unit 20 translate when the teleoperated device is in operation. Linear bearing 51 is securely mounted inside a casing 55 to ensure substantially no relative movement between the liner bearing 51 and the casing 55. The inner cage of two radial bearings 52a, 52b are rotatably mounted on the outer circumference of the linear bearing 51 near its extremities to allow the rotation of the master link 25 about it own longitudinal axis $\theta_1$. A first and a second rod 56a, 56b are mounted transversally through the connecting link 60 of the master unit 20. One extremity of both rods 56a, 56b is configured to receive the inner cage of respective radial bearings 53, 53b that are connected to both side of the casing 55 so that the latter can rotate about the axis $\theta_2$ which intersects the longitudinal axis of the teleoperated surgical device as shown in FIG. 10 about which this device can also rotate and translate as explained above.

More generally, the fourth master link 24 of the teleoperated surgical device according to the invention is rotatable about three different axes $\theta_1$, $\theta_2$, $\theta_3$ intersecting each other at the stationary single point 32' and can further translate along one of the three axes $\theta_1$, $\theta_2$, $\theta_3$ as shown particularly in FIG. 10. Consequently, the corresponding link 15 of the slave unit 10 is rotatable about three different axes $\theta_4$, $\theta_5$, $\theta_6$, which are parallel to the corresponding axis $\theta_1$, $\theta_2$, $\theta_3$, and intersecting each other at the stationary single point 50, and can further translate along one of these three different axes $\theta_4$, $\theta_5$, $\theta_6$.

In a variant, the mechanical constraint means 32 of the teleoperated device comprises a ball-and-socket or spherical joint as schematically shown in FIG. 16b. A through-hole is performed along the diameter of the ball-and-socket joint 70 along which the fourth master link 24 is slidably mounted, optionally inside a linear bearing (not shown). In this configuration, this fourth master link 24 can translate along its longitudinal axis $\theta_1$ and can rotate, through the movement of the ball in its socket, about its longitudinal axis $\theta_1$ and about the second and third axes $\theta_2$, $\theta_3$, which intersect each other in a single point coincident with the geometrical center of the ball.

The seven independent degrees of freedom of the teleoperated device according to this preferred embodiment, as thoroughly described hereafter, provide the desired dexterity needed to perform complicated surgical procedures, such as pulling, cutting and/or suturing tissues. With the aim of being as intuitive as possible, the distal degrees of freedom of both the master and slave units 20, 10 are designed to resemble a simplified human forearm, with an articulated wrist and a distal tool. For example, referring to FIG. 8, the wrist prono-supination is rendered possible through the fourth axial joint 19 of the slave unit 10 whereas the wrist radial-ulnar deviation is rendered possible through the joint 42 of the distal surgical tool 40.

Mechanical transmissions means are partly in the form of pulley-routed flexible elements configured such that each driven pulley of most degree of freedom of the slave unit 10 is connected to the equivalent driving pulley of the master 20 unit, by a single closed cable/tendon loop transmission, as shown in FIG. 17, for the general case of transmitting the motion from a driving pulley Cm of the master unit 20 to a driven pulley Cs of the slave unit 10. This closed cable loop transmission can be composed by a pair of cables, La and Lb, whose both extremities are anchored respectively to the driving and the driven pulley, Cm, Cs to ensure that no relative movement between the cable La, Lb and the pulleys Cm, Cs occurs. Both cables La, Lb form together a single closed loop L from one pulley to the other.

The transmission of the movement between each master pulleys of the master unit 20 and the equivalent slave pulley of the slave unit 10, by using this kind of mechanical transmission, may bring problems of kinematic and dynamic coupling between the driven and the driving pulleys. Furthermore, the adoption of a closed loop cable transmission requires that the overall length of the cable route must be kept constant, for all possible master-slave configurations, independently of the motion performed by the driving pulleys of the master unit 20. Therefore, cables must be routed through joint idler pulleys while maintaining constant cable length. The basics of the cable routing method used is illustrated in FIG. 18 for the general case of having both cables La and Lb, composing the closed loop L, being routed through a general joint. The cables La and Lb are wrapped around a set of pulleys, Im, called the "joint idler pulleys," which are concentric with the joint's axis of revolution. To maintain constant cable length of the closed loop, cables La, Lb must remain in contact with the joint idler pulleys at all times. In this way, if the joint angle $\theta j$ is reduced, the length of the superior segment of La, in contact with the idler pulley Im will decrease and the inferior segment of Lb will increase, by the same value, guaranteeing the constant length of the cable closed loop. In order to keep a permanent contact between the cables La and Lb with the idler pulleys Im, auxiliary pulleys Ap and Ad are added.

Another solution to keep a constant cable length of the closed loop consists in compensating the length change not at the joint level, in the same master or slave unit but between the equivalent idler pulleys Im and Is of respective master and slave units as schematically shown in FIG. 19. In this case, both cables La, Lb are passing under Im and Is and, when the joint angle $\theta j$, $\theta' j$, is changed, the constant length of the closed loop is guaranteed because the increase/reduction of $\theta s$ is compensated by the reduction/increase of $\theta m$.

Figures 20, 21, 22, 23:
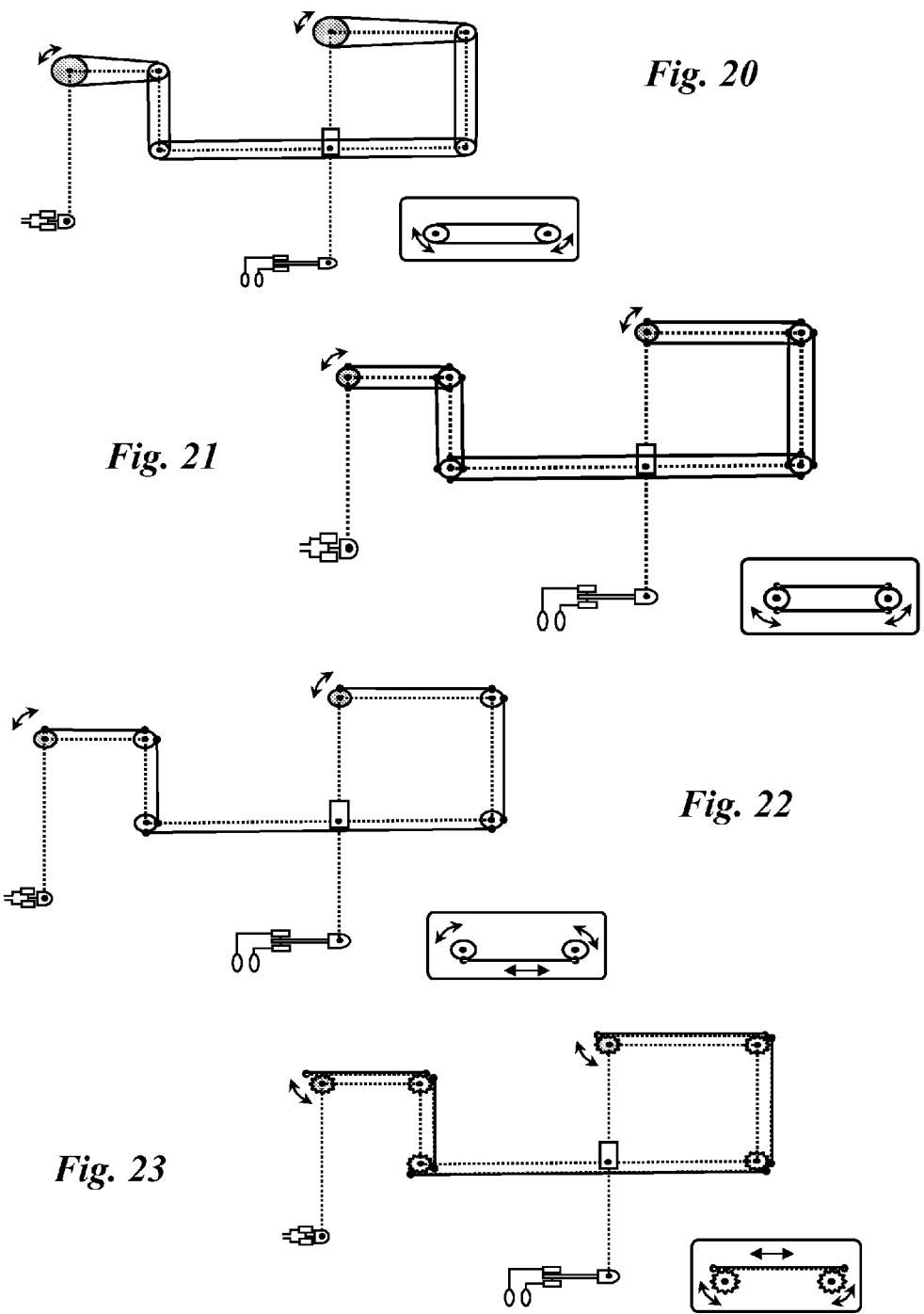
FIG. 20 shows a schematic view of multiple closed cable loops transmission between a general driven pulley of the slave unit and the corresponding driving pulley of the master unit according to another embodiment of the invention.
FIG. 21 shows a schematic view of a double-four-bar system transmission between two general joints (with two Push-Pull Rods) according to another embodiment of the invention.
FIG. 22 shows a schematic view of a single four-bar system transmission between two joints (with only one Push-Pull Rod) according to a further embodiment of the invention.
FIG. 23 shows a schematic view of a transmission using racks and pinions between two general joints according to a yet further embodiment of the invention.

Another alternative consists in splitting the single closed loop in several closed loops, connecting the equivalent master and slave driving and driven pulleys by a set of closed loops joining intermediate idler pulleys as shown in FIG. 20. Cables, belts, chains or other flexible elements can be used for closed loops.

A solution using rigid elements may also be employed, where the transmission is mainly based on articulated linkages, which may guarantee an increased stiffness of the system. FIGS. 21 and 22 show two alternatives where the motion between two general equivalent master and slave joints is transmitted using a set of four bars systems.

Although introducing a significant backlash, ripple and friction to the system, a mechanical transmission using racks and pinions, in the way shown in FIG. 23, might also be employed in some degrees of freedom.

The transmission of movement between joints may also be made through connected rod systems, composed by several rigid transmission elements, articulated between them, sliding over the manipulators links (FIG. 24).

For each degree of freedom of the mechanical teleoperated device according to the preferred embodiment of the invention, different types of mechanical transmission can be used resulting in the same functional outcome. The mechanical transmission means for each of the eight degrees of freedom (one of them is redundant, resulting in seven non-redundant of degrees of freedom) of the teleoperated device are schematically shown from FIG. 25 to FIG. 32.

As shown in FIG. 25, the transmission of motion between the master and slave unit, for the first degree of freedom, is made by the connection link 60, whose axis of rotation is perpendicular and intersects the axes of joints 16 and 26. More particularly, with reference to FIG. 10, the connecting link 60 comprises two radial ball bearings 15a, 25a adapted to receive one or two longitudinal shaft (not shown) of the teleoperated device so that said device is rotatable about the longitudinal axis $\theta_3/\theta_6$.

The transmission of motion between the master and slave unit for the second degree of freedom is shown in FIGS. 10 and 26. The teleoperated device comprises a bar 61 pivotally connected at one extremity to the first slave link 11 of the slave unit 10 and pivotally connected at the other extremity to the first master link 21 of the master unit 20 to ensure that both first slave and master links 11, 21 move parallel to each other when the teleoperated device is operated.

FIG. 27 shows the transmission of motion between the master and slave unit for the third degree of freedom. Joints 17, 27 are connected by a cable 62 (see also FIG. 9) in a single closed loop configuration which runs from a driving pulley C1 connected to the second master link 22 and arranged to rotate about the second shaft 27 of the master unit 20 (FIG. 10) and passing through a set of guiding pulleys p1, p2, p3, p4 up to a driven pulley C'1, connected to the second slave link 12 arranged to rotate about the fifth shaft 17 of the slave unit 10 (FIG. 10) whose axis of rotation is coincident with joint 27.

The transmission of motion between the master and slave unit for the fourth degree of freedom is shown in FIG. 28. Joints 18, 28 are connected by a cable 63 (see also FIG. 9) in a single closed loop configuration which runs from the driving pulley, C2 connected to the third master link 23 (FIG. 8), and arranged to rotate about the third shaft 28 of FIG. 10 of the master unit 20 and passing through a set of guiding pulleys p5, p6, p7, p8, p9, p10 up to the driven pulley C'2, connected to the third slave link 13 (FIG. 8) and arranged to rotate about the sixth shaft 18 of the slave unit 10 (FIG. 10). Auxiliary pulley A1 is used to guarantee the permanent contact between the cable 63 and the set of guiding pulleys guiding pulleys p5, p6, p7, p8, p9, p10.

FIG. 29 shows the transmission of motion between the master and slave unit for the fifth degree of freedom. Joints 19, 29 are connected by a cable 64 (see also FIG. 9) in a single closed loop configuration which runs from the co-axial joint C3, connected to the fourth master link 24 of the of the master unit, and passing through a set of guiding pulleys p11, p12, p13, p14, p15, p16, p17 and p18 up to the co-axial joint C'3, connected to the fourth slave link 24 of the slave unit. Auxiliary pulleys, A2, A3 are used to guarantee the permanent contact between the cable 64 and the set of guiding pulleys p11, p12, p13, p14, p15, p16, p17 and p18.

The transmission of motion between the master and slave unit for the sixth degree of freedom is shown in FIG. 30. Joints 32, 42 are connected by a cable 65 (see also FIG. 9) in a single closed loop configuration which runs from the driving pulley C4, connected to the first handle link 31 of the handle 30, and passing through a set of guiding pulleys p19, p20, p21, p22, p23, and p24 up to the driven pulley C'4, connected to the end-effector link 41 of the end-effector 40. Auxiliary pulleys, A4, A5, A6, A7 are used to guarantee the permanent contact between the cable 65 and the set of guiding pulleys p19, p20, p21, p22, p23, and p24.

FIG. 31 shows the transmission of motion between the master and slave unit for the seventh degree of freedom. Joints 35, 45 are connected by a cable 66 (see also FIG. 9) in a single closed loop configuration which runs from the driving pulley C5, connected to the handle link 33 of the handle 30, and passing through a set of guiding pulleys p25, p26, p2'27, p28, p29, p30, p31, p32, and p33 up to the driven pulley C'5 connected to the first blade 43 of the end-effector 40. Auxiliary pulleys, A8, A9, A10, A11, A12, and A13 are used to guarantee the permanent contact between the cable 66 and the set of guiding pulleys p25, p26, p27, p28, p29, p30, p31, p32, and p33.

Figure 32:
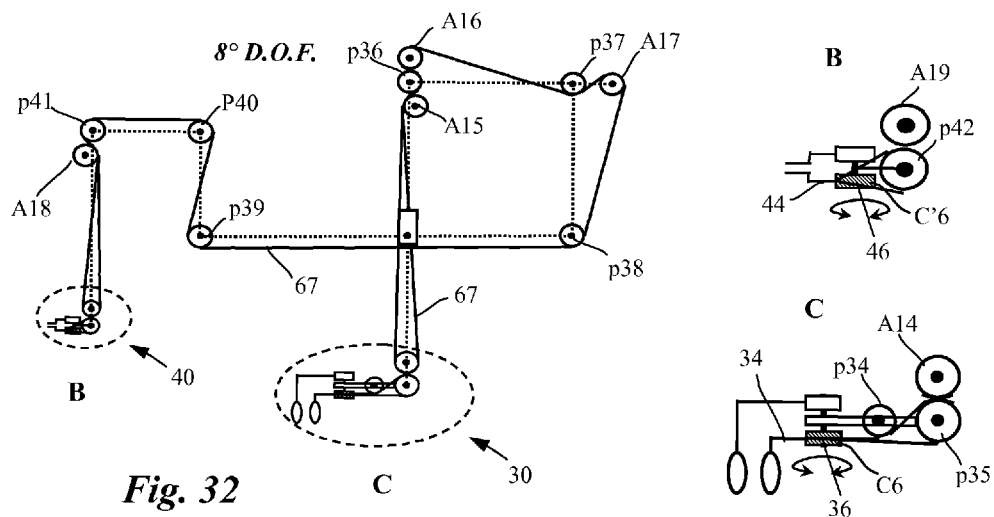

Finally, the transmission of motion between the master and slave unit for the eight degree of freedom is shown in FIG. 32. Joints 36, 46 are connected by a cable 67 (see also FIG. 9) in a single closed loop configuration which runs from the driving pulley C6, connected to the handle link 34 of the handle 30, and passing through a set of guiding pulleys p34, p35, p36, p37, p38, p39, p40, p41 and p42 up to the driven pulley C'6 connected to the second blade 44 of the end-effector 40. Auxiliary pulleys, A14, A15, A16, A17, A18, and A19 are used to guarantee the permanent contact between the cable 67 and the set of guiding pulleys p34, p35, p36, p37, p38, p39, p40, p41 and p42.

When passing through the co-axial joints 29 and 19, cables are not passing through pulleys but twisted around the joint axis. However, due to extensive length of the cables 64, 65 and 66, between driving and driven pulleys, and the short distance between the cables and the axis of rotation, the resulting stretch of the cables is slight, so that the resulting resistance to rotational motion is almost neglectable. The resultant misalignment between the cables and the guiding pulleys is also within reasonable limits, avoiding the cables to jump out of their path.

Figure 33:
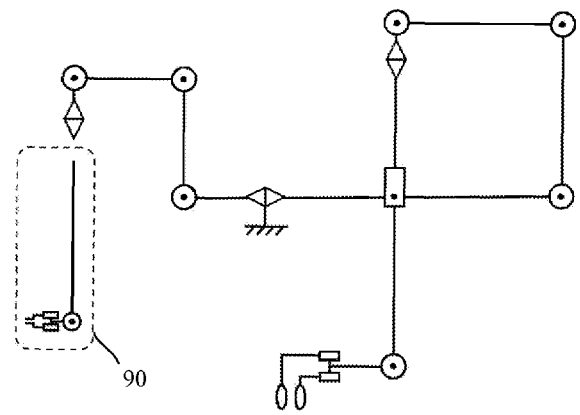
FIG. 33 shows a schematic view of the mechanical teleoperated device with a detachable tool.
Figure 33A:
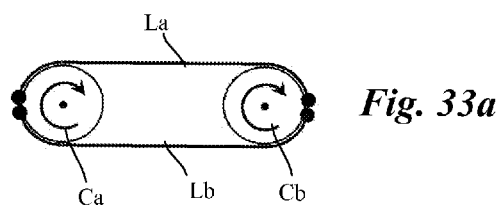
FIG. 33a shows a schematic view of single cable loop transmission.
Figure 33B:
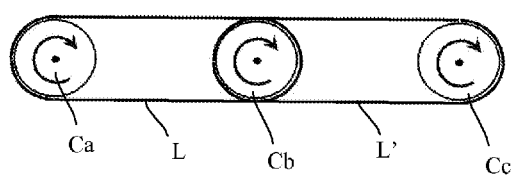
FIG. 33b shows a schematic view of double cable loops transmission.

Each one of the cable loops 64, 65 and 66 can also be divided in two cable loops if the distal degrees of freedom of the slave unit are detachable, 90, from the proximal part of the teleoperated device, as exemplified in FIG. 33. In this way, instead of a single cable loop from the driving pulley Ca to the driven pulley Cb which is composed by two cables La, Lb (FIG. 33a), the motion is transmitted by two cable loops: one from Ca to Cc, loop L, and the other from Cc to Cb, loop L', as shown in FIG. 33b.

The kinematic model of the master and slave manipulators may also take different configurations and different number of degrees of freedom, keeping the same principle of working. FIGS. 34 and 35 show some other possible kinematic configurations for both the master and slave unit, which may originate different transmission layouts.

In some embodiments, torsion springs 16a, 17a, 18a, 26a, 27a, 28a are mounted on the teleoperated device, as shown in FIG. 36, to connect the master and slave links with the corresponding master and slave joints in order to reduce, or eliminate, the effects of the gravity on the teleoperated device, to increase the haptic transparency of the telemanipulation. In some embodiments, as shown in FIG. 37, counterweights 16a, 17a, 18a, 26a, 27a, 28a are connected to some links of the master and slave units, bringing the total center of mass of each slave and master unit to a region close to the point of intersection 16, 26 between the axes of the first two degrees of freedom.

In some embodiments, the mechanical teleoperated device comprises brake means in the four joints of the mechanical constraint 32, allowing the telemanipulator to be fixed in several positions of its workspace, when the surgeon is not holding the handle.

In some embodiments, the mechanical teleoperated device comprises force sensors capable of measuring the forces exerted on the moving links and/or position sensors capable of measuring the movement of the different joints, in order to allow a reconstruction of the movement of the entire teleoperated device.

Although the mechanical teleoperated device according to the invention has been described for performing minimally invasive surgical procedures, it may also be used for other forms of endoscopic surgery as well as open surgery or procedures on MRi environments, by using MRi compatible materials. Fields like ophthalmology, brain surgery, orthopedics and dentistry should also be targets for this invention.

The mechanical teleoperated device according to the invention could also be employed for any suitable remote actuated application requiring a dexterous manipulation with high stiffness, precision and quality force feedback—like assembly manipulation, manipulation in narrow places, manipulation in dangerous or difficult environments, and manipulation in contaminated or clean environments. In this configuration, the surgical tool is replaced by a suitable multi-articulated holder or gripper.

Moreover, while this invention has been particularly shown and described with references to a preferred embodiment thereof, it will be understood by those skilled in the art that various changes in form and details may be made therein without departing from the spirit and scope of the invention as defined by the appended claims. For instance, the second and third axes $\theta_2$, $\theta_3$ about which the guided master link is rotatable are not necessarily perpendicular to each other provided that the longitudinal axis $\theta_1$ of the guided master link and these second and third axes $\theta_2$, $\theta_3$ intersect each other at a stationary single point.

The invention claimed is:

1. A mechanical teleoperated device for remote manipulation comprising: at least one mechanical teleoperated device using fully mechanical motion transmission comprising: a slave unit having a number of slave links interconnected by a plurality of slave joints; an end-effector connected to a distal end of the slave unit; a master unit having a corresponding number of master links interconnected by a plurality of master joints; a handle connected to a distal end of the master unit for operating the mechanical teleoperated device; at least one first mechanical transmission device arranged to kinematically connect the slave unit with the master unit such that movement applied on each of the plurality of master joints of the master unit is reproduced by a corresponding respective one of the plurality of slave joints of the slave unit; at least one second mechanical transmission device arranged to kinematically connect the end-effector with the handle such that movements applied on the handle are reproduced by the end-effector; and mechanical constraint device configured to ensure that one master link of the master unit is guided along its longitudinal axis so that a corresponding slave link of the slave unit always translates along a virtual axis parallel to the longitudinal axis of a guided master link in a vicinity of the remote manipulation when the mechanical teleoperated device is operated; wherein the mechanical teleoperated device is configured to enable the guided master link of the master unit to rotate about its longitudinal axis, and about a second and a third axis, which longitudinal axis of the guided master link and which second and third axis always intersect each other at a stationary single point independently of an orientation of the guided master link to enable the corresponding slave link of the slave unit to rotate about its longitudinal axis, and about a fifth and sixth virtual axis which are parallel respectively to the second and third axis; wherein a longitudinal axis of the corresponding slave link and the fifth and sixth virtual axes always intersect each other at a remote-center-of-motion in the vicinity of the remote manipulation; and wherein a kinematic model of a chain formed by the number of slave links and corresponding respective slave joints of the slave unit is identical to the kinematic model of the chain formed by the corresponding number of master links and corresponding respective master joints of the master unit.

2. The mechanical teleoperated device according to claim 1, wherein the end-effector comprises a plurality of at least two end-effector links interconnected by end-effector joints and wherein the handle comprises a corresponding plurality of at least two corresponding handle links interconnected by handle joints.

3. The mechanical teleoperated device according to claim 2, wherein the kinematic model of the chain formed by a plurality of end-effector links and a plurality of corresponding end-effector joints of the end-effector is identical to the kinematic model of the chain formed by a plurality of handle links and a plurality of corresponding handle joints of the handle.

4. The mechanical teleoperated device according to claim 2, wherein an amplitude of a movement applied on each handle link of the handle is reproduced by a corresponding end-effector link of the end-effector at a first predetermined scale ratio which corresponds to a ratio between a length of each end-effector link and a length of the corresponding handle link.

5. The mechanical teleoperated device according to claim 1, wherein an amplitude of a movement of each master link of the master unit, when the mechanical teleoperated device is operated, is reproduced by a corresponding slave link of the slave unit at a second predetermined scale ratio which corresponds to a ratio between a length of each slave link and a length of each corresponding master link.

6. The mechanical teleoperated device according to claim 1, wherein the slave and master units are connected together by a connecting link adapted to rotate about its longitudinal axis which is aligned with the stationary single point and the remote-center-of-motion independently of an orientation of the connecting link.

7. The mechanical teleoperated device according to claim 6, wherein the master unit comprises at least three links arranged to form a polygon construction of at least four sides with the connecting link, wherein one of the second and third axes is perpendicular to a plane defined by the polygon construction.

8. The mechanical teleoperated device according to claim 6, wherein the master unit comprises a first master link connected to a first master joint at one extremity and extending upwardly and perpendicularly with reference to the connecting link, when the mechanical teleoperated device is in a neutral position, to be connected to a second master joint at its other extremity, a second master link connected to the second master joint at one extremity and extending to be connected to a third master joint at its other extremity, a third master link connected to the third master joint at one extremity and to a fourth master joint at its other extremity, wherein one extremity of the guided master link is connected to the fourth master joint such that the guided master link is axially rotatable about its longitudinal axis and extends downwardly across the connecting link through the mechanical constraint device, the other extremity of the guided master link being connected to the handle of the mechanical teleoperated device.

9. The mechanical teleoperated device according to claim 8, wherein the handle of the mechanical teleoperated device comprises a first handle link which is connected to one extremity of the guided master link through a first handle joint, wherein an axis of rotation of the first handle link is perpendicular and intersecting to the longitudinal axis of the guided master link, the handle further comprising a second and third handle link connected to the first handle link through respectively a second and third handle joint coaxially mounted to each other.

10. The mechanical teleoperated device according to claim 9 wherein the slave unit comprises a first slave joint connected to one extremity of the connecting link, a first slave link connected to the first slave joint at one extremity and extending upwardly and perpendicularly with reference to the connecting link, when the teleoperated device is in a neutral position, to be connected to a second slave joint at its other extremity, a second slave link connected to the second slave joint at one extremity and extending to be connected to a third slave joint at its other extremity, a third slave link connected to the third slave joint at one extremity and to a fourth slave joint at its other extremity, wherein the fourth slave joint is coupled with a fourth slave link so that the fourth slave link is axially rotatable about its longitudinal axis and extends downwardly.

11. The mechanical teleoperated device according to claim 10, wherein the end-effector comprises a first end-effector link which is connected at one extremity of the fourth slave link through a first end-effector joint, the axis of rotation of the first end-effector link being perpendicular to and intersecting the longitudinal axis of the fourth slave link, wherein the end-effector further comprises a second and third end effector link or blade connected to the first end-effector link through respectively a second and third end-effector joint coaxially mounted to each other.

* * * * *